United States Patent
Urech et al.

(10) Patent No.: US 10,077,312 B2
(45) Date of Patent: Sep. 18, 2018

(54) CD3 AND IL-23 RECEPTOR BINDING BISPECIFIC CONSTRUCTS AND THEIR USE IN THE TREATMENT OF VARIOUS DISEASES

(71) Applicant: NUMAB AG, Waedenswil (CH)

(72) Inventors: David Urech, Jona (CH); Tea Gunde, Zurich (CH); Sebastian Meyer, Eggenwil (CH)

(73) Assignee: Numab Therapeutics AG, Pfaeffikon (CH)

( * ) Notice: Subject to any disclaimer, the term of this patent is extended or adjusted under 35 U.S.C. 154(b) by 0 days.

(21) Appl. No.: 14/889,225

(22) PCT Filed: May 12, 2014

(86) PCT No.: PCT/EP2014/001282
§ 371 (c)(1),
(2) Date: Nov. 5, 2015

(87) PCT Pub. No.: WO2014/180577
PCT Pub. Date: Nov. 13, 2014

(65) Prior Publication Data
US 2016/0083473 A1    Mar. 24, 2016

(30) Foreign Application Priority Data
May 10, 2013  (EP) .................................... 13002500

(51) Int. Cl.
*C07K 16/28* (2006.01)
*A61K 39/395* (2006.01)

(52) U.S. Cl.
CPC ...... *C07K 16/2866* (2013.01); *C07K 16/2809* (2013.01); *C07K 2317/31* (2013.01); *C07K 2317/33* (2013.01); *C07K 2317/55* (2013.01); *C07K 2317/56* (2013.01); *C07K 2317/569* (2013.01); *C07K 2317/622* (2013.01); *C07K 2317/626* (2013.01); *C07K 2317/73* (2013.01); *C07K 2317/75* (2013.01); *C07K 2317/92* (2013.01)

(58) Field of Classification Search
None
See application file for complete search history.

(56) References Cited

U.S. PATENT DOCUMENTS

2007/0065437 A1* 3/2007 Elson .................. A61K 9/0019
                                                     424/144.1
2010/0135998 A1* 6/2010 Bowman .............. A61K 31/55
                                                     424/133.1

FOREIGN PATENT DOCUMENTS

WO    1999/54440 A1    10/1999
WO    2008/106134 A2    9/2008

OTHER PUBLICATIONS

McKarns et al., "TGF-beta 1 differentially regulates IL-2 expression and [3H]-thymidine incorporation in CD3 epsilon mAb- and CD28 mAbactivated splenocytes and thymocytes.", IMM Unopharmacology, val. 48, No. 2, Jul. 1, 2000 (Jul. 1, 2000), pp. 101-115.
Leo R. Fitzpatrick: "Novel Pharmacological Approaches for Inflammatory Bowel Disease: Targeting Key Intracellular Pathways and the IL-23/IL-17 Axis", International Journal of Inflammation, val. 9, No. 4, Jan. 1, 2012 (Jan. 1, 2012), pp. 652-658.
Chunlei Tang et al., "Interleukin-23: as a drug target for autoimmune inflammatory diseases", Immunology, val. 135, No. 2, Feb. 11, 2012 (Feb. 11, 2012), pp. 112-124.
Cayatte et al., "Biomarkers of Therapeutic Response in the IL-23 Pathway in Inflammatory Bowel Disease", Clinical and Translational Gastroenterology, val. 3, No. 2, Feb. 1, 2012 (Feb. 1, 2012), p. el 0.
Yi et al., "Anti-IL-23 therapy inhibits multiple inflammatory pathways and ameliorates autoimmune encephalomyelitis", Journal of Clinical Investigation, American Society for Clinical Investigation, US, val. 116, No. 5, May 1, 2006 (May 1, 2006), pp. 1317-1326.
Lee et al., "The IL-23-MDL-1 axis in innate cell driven auto reactivity"; "J3 2020" In: Chen Dong, Tadamitsu Kishimoto and Richard A. Flavell: "Inflammatory Diseases: Recent Advances in Basic and Translational Research and Therapeutic Treatments (J4)", Jan. 17, 2014 (Jan. 17, 2014), Keystone Symposia on Molecular and Cellular Biology.
International Search Report and Written Opinion dated Jul. 28, 2014 in PCT/EP2014/001282 (15 pages).
Extended European Search Report dated Nov. 7, 2013 in EP 13002500.0 (10 pages).

* cited by examiner

*Primary Examiner* — Elly-Gerald Stoica
(74) *Attorney, Agent, or Firm* — Prismatic Law Group PLLC

(57) ABSTRACT

The present invention relates to bispecific constructs that specifically bind to immune effector cells and, simultaneously, to IL23R-carrying target cells, as well as nucleic acids, vectors, host cells, pharmaceutical compositions, and methods of production and use thereof, including such bispecific constructs for use in treating inflammatory and/or autoimmune diseases and/or cancer.

18 Claims, 7 Drawing Sheets

Figure 1:
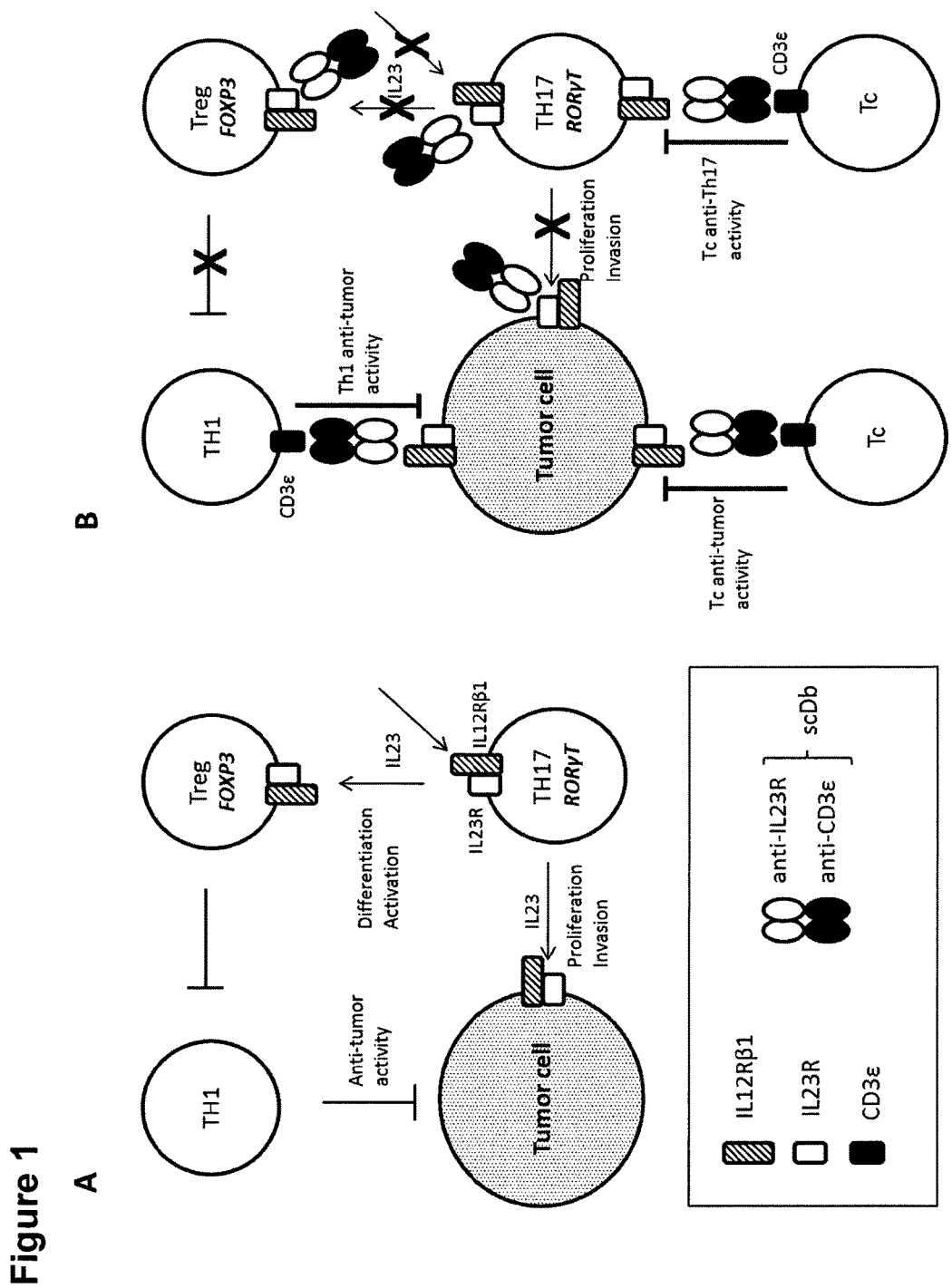

Specification includes a Sequence Listing.

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: synthetic peptide linker

<400> SEQUENCE: 1

Gly Gly Gly Gly Ser
1               5

<210> SEQ ID NO 2
<211> LENGTH: 20
<212> TYPE: PRT
<213> ORGANISM: Artificial Sequence
<220> FEATURE:
<223> OTHER INFORMATION: snythetic peptide linker

<400> SEQUENCE: 2

Gly Gly Gly Gly Ser Gly Gly Gly Gly Ser Gly Gly Gly Gly Ser Gly
1               5                   10                  15

Gly Gly Gly Ser
            20

<210> SEQ ID NO 3
<211> LENGTH: 113
<212> TYPE: PRT
<213> ORGANISM: Artificial Sequence
<220> FEATURE:
<223> OTHER INFORMATION: VL anti-IL23R 14-11-D07-sc01

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

```
Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly

<210> SEQ ID NO 4
<211> LENGTH: 121
<212> TYPE: PRT
<213> ORGANISM: Artificial Sequence
<220> FEATURE:
<223> OTHER INFORMATION: VH anti-IL23R 14-11-D07-sc01

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Asn Ser Asn
            20                  25                  30

Tyr Tyr Met Cys Trp Val Arg Gln Ala Pro Gly Lys Gly Leu Glu Trp
        35                  40                  45

Ile Gly Cys Ile Tyr Val Gly Ser His Val Asn Thr Tyr Tyr Ala Asn
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120

<210> SEQ ID NO 5
<211> LENGTH: 114
<212> TYPE: PRT
<213> ORGANISM: Artificial Sequence
<220> FEATURE:
<223> OTHER INFORMATION: VL anti-CD3  clone 6

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Gln Ser Ser Glu Ser Val Tyr Asn Asn
            20                  25                  30

Lys Arg Leu Ser Trp Tyr Gln Gln Lys Pro Gly Lys Ala Pro Lys Leu
        35                  40                  45

Leu Ile Tyr Thr Ala Ser Ser Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Glu Phe Thr Cys
                85                  90                  95
```

```
Ser Asn Ala Asp Cys Phe Thr Phe Gly Gln Gly Thr Lys Leu Thr Val
                100                 105                 110

Leu Gly

<210> SEQ ID NO 6
<211> LENGTH: 123
<212> TYPE: PRT
<213> ORGANISM: Artificial Sequence
<220> FEATURE:
<223> OTHER INFORMATION: VH anti-CD3 clone 6

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Ser Ser Tyr
            20                  25                  30

Ala Met Ile Trp Val Arg Gln Ala Pro Gly Lys Gly Leu Glu Trp Ile
        35                  40                  45

Gly Met Ile Leu Arg Ala Gly Asn Ile Tyr Tyr Ala Ser Trp Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Arg His Tyr Asn Arg Glu Gly Tyr Pro Ile Gly Ile Gly Asp Leu
            100                 105                 110

Trp Gly Gln Gly Thr Leu Val Thr Val Ser Ser
        115                 120

<210> SEQ ID NO 7
<211> LENGTH: 501
<212> TYPE: PRT
<213> ORGANISM: Artificial Sequence
<220> FEATURE:
<223> OTHER INFORMATION: PRO165

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Gly Ser Glu Val Gln Leu Val Glu Ser Gly Gly Gly
        115                 120                 125

Leu Val Gln Pro Gly Gly Ser Leu Arg Leu Ser Cys Ala Ala Ser Gly
    130                 135                 140

Phe Pro Leu Ser Ser Tyr Ala Met Ile Trp Val Arg Gln Ala Pro Gly
145                 150                 155                 160
```

```
Lys Gly Leu Glu Trp Ile Gly Met Ile Leu Arg Ala Gly Asn Ile Tyr
                165                 170                 175
Tyr Ala Ser Trp Val Lys Gly Arg Phe Thr Ile Ser Arg Asp Asn Ser
            180                 185                 190
Lys Asn Thr Val Tyr Leu Gln Met Asn Ser Leu Arg Ala Glu Asp Thr
        195                 200                 205
Ala Val Tyr Tyr Cys Ala Arg Arg His Tyr Asn Arg Glu Gly Tyr Pro
    210                 215                 220
Ile Gly Ile Gly Asp Leu Trp Gly Gln Gly Thr Leu Val Thr Val Ser
225                 230                 235                 240
Ser Gly Gly Gly Gly Ser Gly Gly Gly Gly Ser Gly Gly Gly Gly Ser
                245                 250                 255
Gly Gly Gly Gly Ser Asp Ile Gln Met Thr Gln Ser Pro Ser Ser Leu
                260                 265                 270
Ser Ala Ser Val Gly Asp Arg Val Thr Ile Thr Cys Gln Ser Ser Glu
            275                 280                 285
Ser Val Tyr Asn Asn Lys Arg Leu Ser Trp Tyr Gln Gln Lys Pro Gly
        290                 295                 300
Lys Ala Pro Lys Leu Leu Ile Tyr Thr Ala Ser Ser Leu Ala Ser Gly
305                 310                 315                 320
Val Pro Ser Arg Phe Ser Gly Ser Gly Ser Gly Thr Asp Phe Thr Leu
                325                 330                 335
Thr Ile Ser Ser Leu Gln Pro Glu Asp Phe Ala Thr Tyr Tyr Cys Gln
                340                 345                 350
Gly Glu Phe Thr Cys Ser Asn Ala Asp Cys Phe Thr Phe Gly Gln Gly
            355                 360                 365
Thr Lys Leu Thr Val Leu Gly Gly Gly Gly Ser Glu Val Gln Leu
        370                 375                 380
Val Glu Ser Gly Gly Gly Leu Val Gln Pro Gly Gly Ser Leu Arg Leu
385                 390                 395                 400
Ser Cys Ala Ala Ser Gly Ile Asp Phe Asn Ser Asn Tyr Tyr Met Cys
                405                 410                 415
Trp Val Arg Gln Ala Pro Gly Lys Gly Leu Glu Trp Ile Gly Cys Ile
            420                 425                 430
Tyr Val Gly Ser His Val Asn Thr Tyr Tyr Ala Asn Trp Ala Lys Gly
        435                 440                 445
Arg Phe Thr Ile Ser Arg Asp Asn Ser Lys Asn Thr Val Tyr Leu Gln
    450                 455                 460
Met Asn Ser Leu Arg Ala Glu Asp Thr Ala Val Tyr Tyr Cys Ala Thr
465                 470                 475                 480
Ser Gly Ser Ser Val Leu Tyr Phe Lys Phe Trp Gly Gln Gly Thr Leu
                485                 490                 495
Val Thr Val Ser Ser
                500
```

CD3 AND IL-23 RECEPTOR BINDING BISPECIFIC CONSTRUCTS AND THEIR USE IN THE TREATMENT OF VARIOUS DISEASES

CROSS REFERENCE TO RELATED APPLICATIONS

The present invention is filed under 35 U.S.C. § 371 as the U.S. national phase of International Application No. PCT/EP2014/001282, filed May 12, 2014, which designated the U.S. and claims the benefit of priority to European Patent Application No. 13002500.0, filed May 10, 2013, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Oct. 28, 2015, is named N0002USNP_SeqListing.txt and is 10 kilobytes in size.

FIELD OF THE INVENTION

The present invention relates to bispecific constructs that specifically bind to immune effector cells and, simultaneously, to IL23R-carrying target cells, as well as nucleic acids, vectors, host cells, pharmaceutical compositions, and methods of production and use thereof, including such bispecific constructs for use in treating inflammatory and/or autoimmune diseases and/or cancer.

BACKGROUND OF THE INVENTION

Interleukin (IL)-23 is a heterodimeric cytokine comprised of two protein subunits, designated p40 and p19 for their approximate molecular weights. The p40 protein is shared between IL-12 and IL-23, whereas the p19 protein subunit is unique to IL-23. IL-23 signals through a two-chain receptor complex consisting of the IL-12 receptor beta-1 (IL-12Rβ1) chain, which binds to p40, and a unique IL-23 receptor chain (IL23R), which confers IL-23-specific intracellular signaling.

IL-23 induces the differentiation of naïve $CD4^+$ T cells into pathogenic IL-17-producing helper T (Th17 or $Th_{IL-17}$) cells. The IL-17 secreted by this distinct helper T cell subset is an important effector cytokine during inflammation. Elevated IL-17 levels have been observed in target tissues of various autoimmune diseases and inflammatory conditions, including rheumatoid arthritis, inflammatory bowel diseases (i.e., Crohn's disease and ulcerative colitis), and psoriasis. Therefore, IL-23 has been implicated as a critical factor in inflammatory conditions and autoimmune-mediated diseases.

Several approaches to target IL-23/IL-17 signaling have been tested so far, including antibodies directed against IL-23 or the IL-23 receptor, as potential therapeutic approaches for treating inflammatory and autoimmune diseases. With respect to the use of IL-23 as a target for potential pharmacological interventions, various neutralizing antibodies directed to the p40 subunit of IL-23 have been developed for potential use in the treatment of autoimmune driven diseases. For example, the monoclonal antibody known as "ustekinumab" (Janssen-Cilag) is an antibody that targets the common p40 subunit of IL-12 and IL-23. It has been shown to be effective in the treatment of psoriasis and psoriatic arthritis. Another monoclonal antibody that targets the smaller p19 subunit of IL-23 is described in EP 2 548 577.

With regard to strategies aimed at blocking the IL-23 receptor function by IL-23 receptor-targeting antibodies, WO 2004/042009 discloses the use of a monoclonal anti-IL-23 receptor antibody or fragments thereof (Fv, Fab, Fab' and $F(ab')_2$) for the treatment of an inflammatory disease associated with elevated expression of IL-17. Moreover, WO 2008/106134 discloses the generation of humanized antibodies, which recognize the IL23R chain of the human IL-23 receptor, suitable for use in the treatment of inflammatory and autoimmune disorders. These anti-IL23R antibodies include, inter alia, antibodies conjugated to cytotoxic payloads that can be used in immunotherapy to selectively target and kill cells expressing IL23R on their surface.

A promising approach for the antibody-based treatment of various cancer diseases is the redirection of immune effector cells to specifically lyse target cells using bispecific antibodies. The bispecific antibodies recognize a particular antigen on the surface of a target cell and, simultaneously, an activating surface molecule of an immune effector cell, such as a natural killer (NK) cell or a cytotoxic T (Tc) cell, to thereby kill the target cells.

The bispecific antibody concept is, for example, used in cancer therapy where bispecific antibodies are employed that bind to a cancer antigen on cancer cells and, simultaneously, to the epsilon chain of CD3 presented on, for example, cytotoxic T cells. A well-known example of such a bispecific antibody construct is "blinatumomab", an antibody in the BiTE (bi-specific T cell engager) format, for the treatment of non-Hodgkin's lymphoma and acute lymphoblastic leukemia. Blinatumomab was developed by Micromet and simultaneously binds to the cancer antigen CD19 as well as to CD3 on the surface of cytotoxic T cells, thereby linking these two cell types together and activating the cytotoxic T cell to lyse the target cancer cell.

The hitherto most successful antibody-based approaches to treat inflammatory and/or autoimmune diseases exploit mechanisms of action that interfere with the interaction of cytokines and their respective receptors in order to prevent signaling through cytokine receptors. Examples include inhibition of TNFα (e.g., infliximab and adalimumab), inhibition of p40 (e.g., ustekinumab) or inhibition of IL6R (e.g., tocilizumab). However, these antibodies often still allow for the signaling through redundant pathways. As a consequence, a significant number of patients cannot be effectively treated. For example, up to 40% of the patients are refractory to treatment with TNFα inhibiting antibodies.

Thus, there is still a need for new and improved treatment strategies in the treatment of various diseases, such as inflammatory and/or autoimmune diseases and cancer. In particular, bispecific molecules for use in such treatments are required that are stable, easy to produce, highly specific for a given target antigen, and have a low immunogenicity.

SUMMARY OF THE INVENTION

The present invention meets the needs presented above by providing a bispecific construct that specifically binds to an immune effector cell, i.e. a cytotoxic effector T (Tc) cell and, simultaneously, to a IL-23 receptor expressing target cell, e.g. a pathogenic IL-17-producing helper T cell (Th17 cell), in order to kill the IL-23 receptor expressing target cell.

In a first aspect, the present invention provides a bispecific construct comprising at least one first binding moiety and at least one second binding moiety for use in the treatment of cancer comprising IL23R-expressing tumor cells, wherein said first binding moiety specifically binds to a first antigen present on a cytotoxic effector T (Tc) cell, and said second binding moiety specifically binds to the IL-23 receptor specific subunit (IL23R).

In a second aspect, the present invention provides a bispecific construct comprising at least one first binding moiety and at least one second binding moiety, wherein said first binding moiety specifically binds to a first antigen present on a cytotoxic effector T (Tc) cell, and said second binding moiety specifically binds to the IL-23 receptor specific subunit (IL23R) present on the surface of a target cell.

The present invention also provides, in further aspects, a nucleic acid or nucleic acids encoding the bispecific construct of the present invention, as well as a vector or vectors comprising said nucleic acid or nucleic acids, and a host cell or host cells comprising said vector or vectors.

Another aspect the present invention relates to a method for producing the bispecific construct of the present invention, comprising (i) providing a nucleic acid or nucleic acids according to the present invention, or a vector or vectors according to the present invention, expressing said nucleic acid or nucleic acids or said vector or vectors and collecting said bispecific construct from the expression system, or (ii) providing a host cell or host cells of the present invention, culturing said host cell or host cells, and collecting the bispecific construct from the cell culture.

Yet another aspect of the present invention relates to a pharmaceutical composition comprising the bispecific construct of the present invention and a pharmaceutically acceptable carrier.

In still another aspect, the present invention relates to the use of a bispecific construct of the present invention in the treatment of an inflammatory and/or autoimmune disease, or in a method for the treatment of an inflammatory and/or autoimmune disease, comprising administering to a subject an effective amount of the bispecific construct of the present invention. Exemplary inflammatory and/or autoimmune diseases include rheumatoid arthritis, ankylosing spondylitis, psoriasis, psoriatic arthritis, ulcerative colitis, Crohn's disease, systemic lupus erythematosus, juvenile diabetes, autoimmune uveitis, multiple sclerosis, Parkinson's disease, Alzheimer's disease, and ischemia-reperfusion injury.

Particular embodiments of the present invention are set forth in the appended dependent claims.

FIGURES

FIG. 1: A: IL23 signaling and Th1 antitumor response; B: proposed mechanisms of bispecific anti-IL23RxCD3ε antibody interactions.

Figure 2:
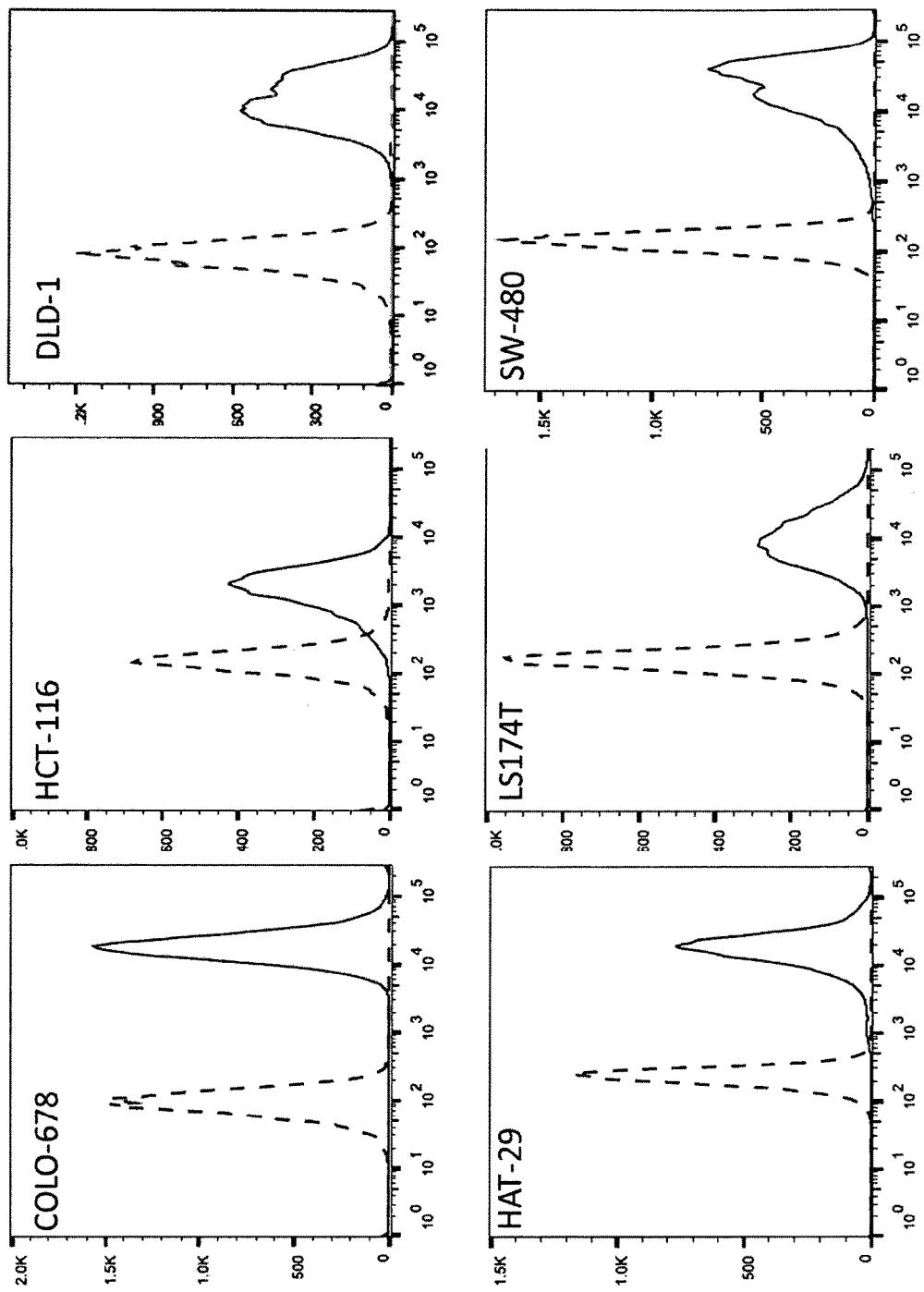

FIG. 2: Expression of IL23R on colon cancer cell-lines. IL23R expression was detected by a primary goat polyclonal anti-IL23R antibody and a PE-labeled anti-goat antibody. Solid lines, IL23R expression; dashed lines, isotype control. X-axis, PE intensity; Y-axis, cell counts.

Figure 3:
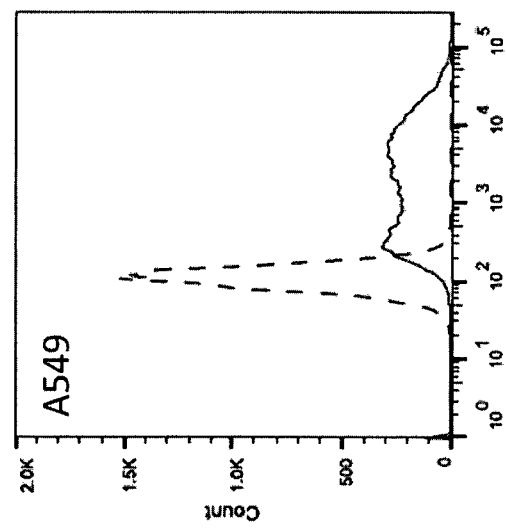

FIG. 3: IL23R expression on lung adenocarcinoma cell-line. IL23R expression was detected by a primary goat polyclonal anti-IL23R antibody and a PE-labeled anti-goat antibody. Solid lines, IL23R expression; dashed lines, isotype control. X-axis, PE intensity; Y-axis, cell counts.

Figure 4:
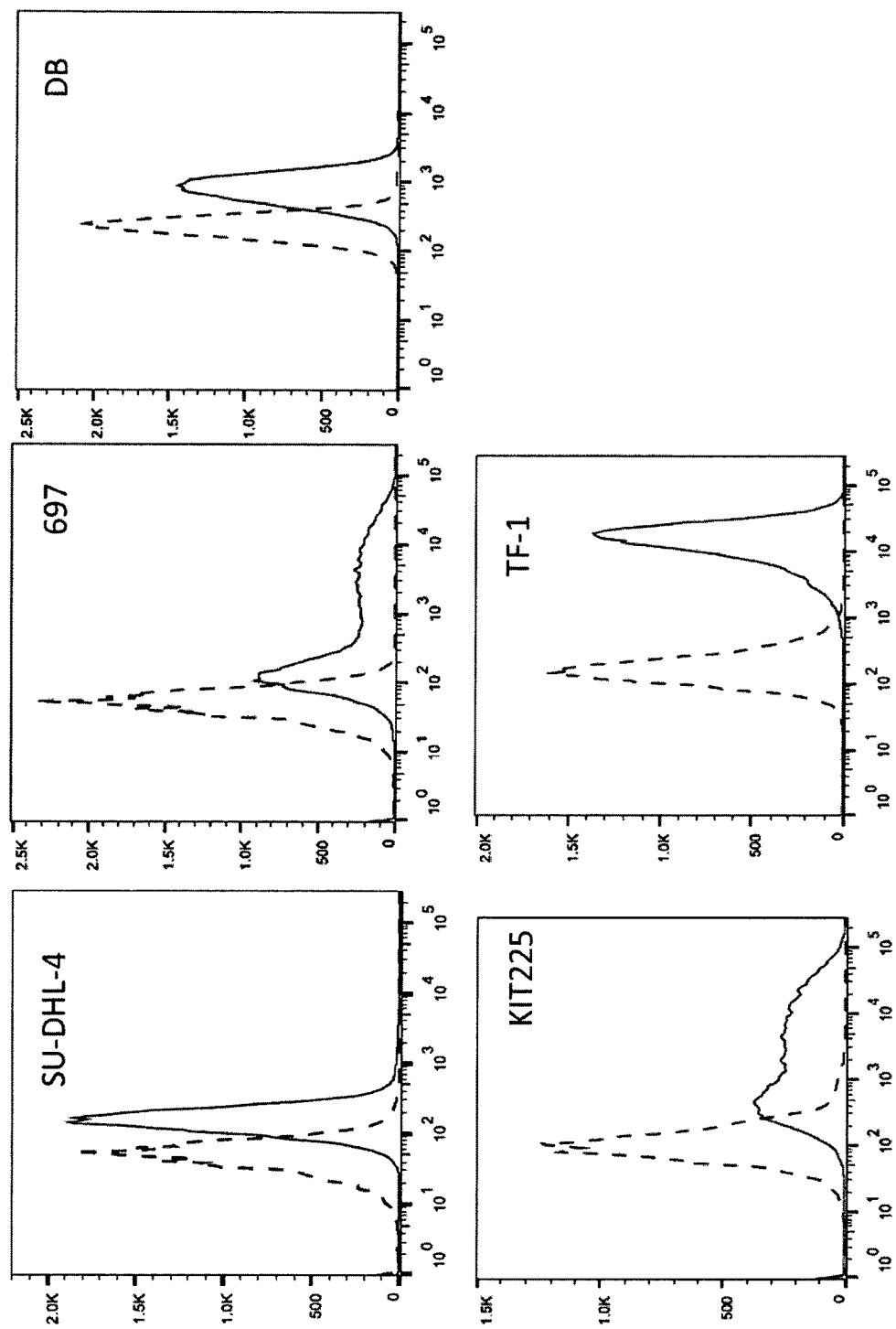

FIG. 4: IL23R expression on lymphoma/leukemia cell-lines. IL23R expression was detected by a primary goat polyclonal anti-IL23R antibody and a PE-labeled anti-goat antibody. Solid lines, IL23R expression; dashed lines, isotype control. X-axis, PE intensity; Y-axis, cell counts.

Figure 5:
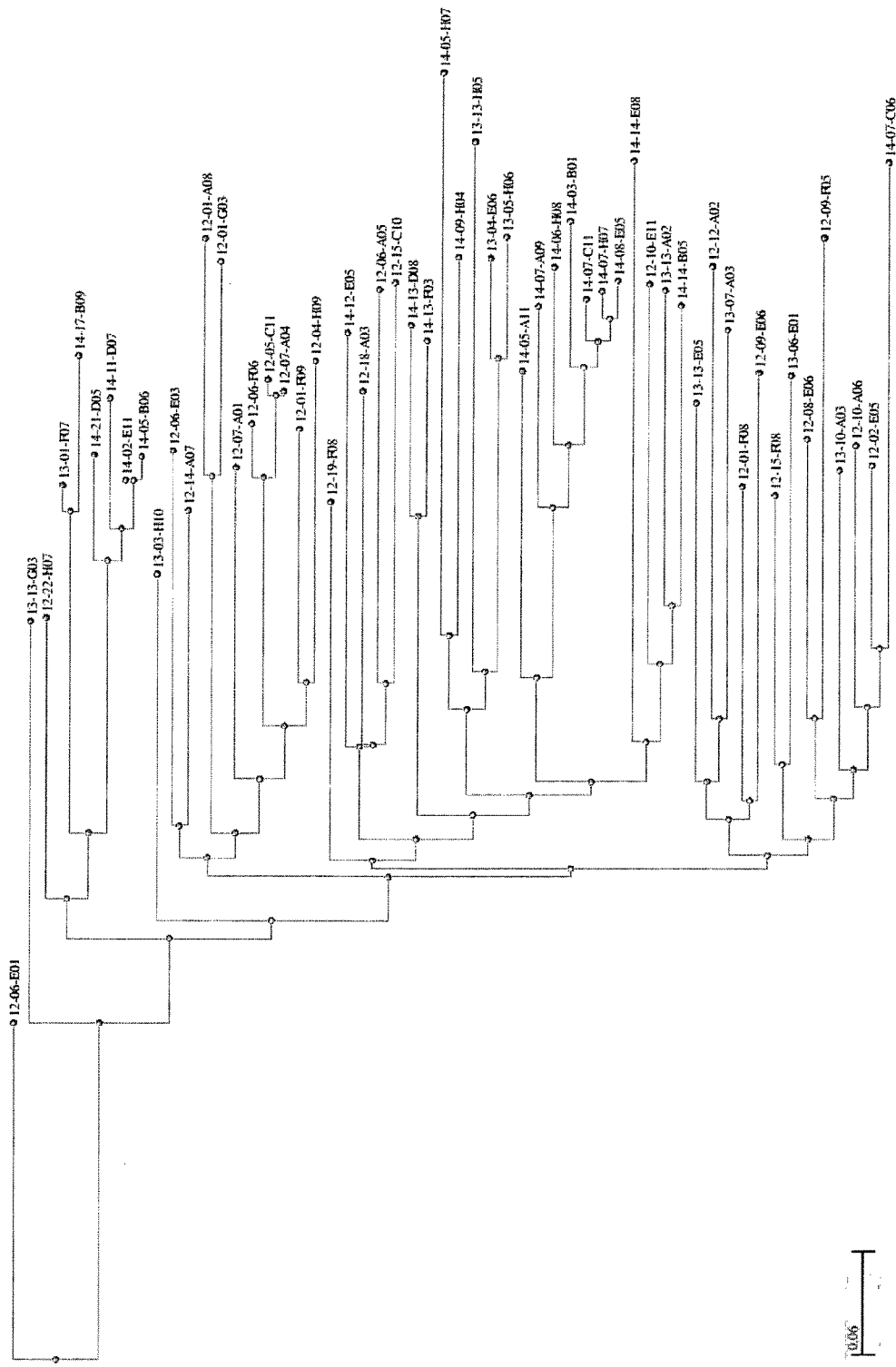

FIG. 5: Phylogenetic tree generated by aligning the unique CDR sets with the Neighbor Joining algorithm of COBALT.

Figure 6:
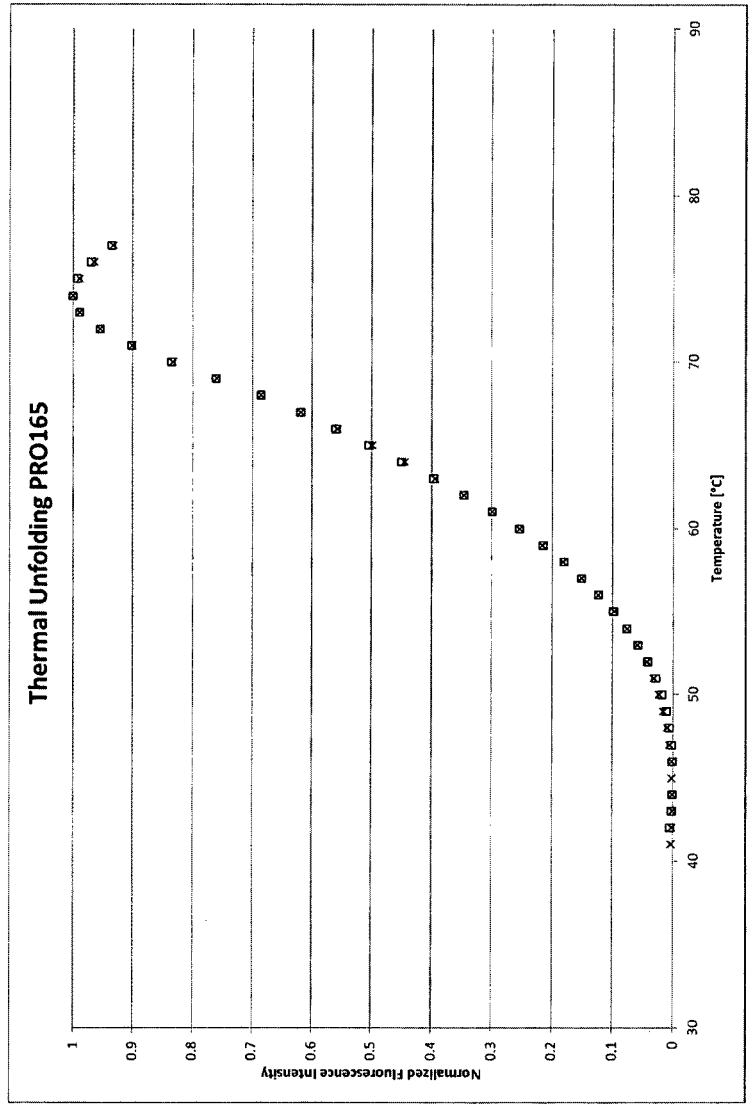

FIG. 6: Thermal unfolding of PRO165 by differential scanning fluorimetry. Duplicate measurement of temperature induced protein unfolding normalized fluorescence signal.

Figure 7:
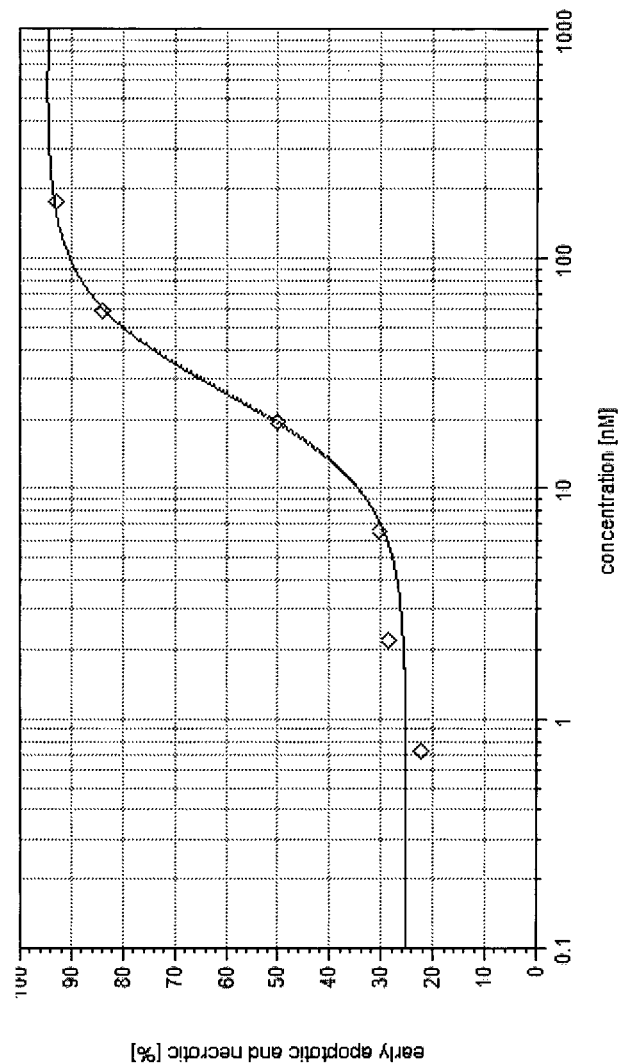

FIG. 7. T cell driven lysis of DLD-1 colon carcinoma cells induced by PRO165. Quantification of early apoptotic and necrotic DLD-1 cells.

DETAILED DESCRIPTION OF THE INVENTION

In a first aspect, the present invention provides a bispecific construct comprising at least one first binding moiety and at least one second binding moiety for use in the treatment of cancer comprising IL23R-expressing tumor cells, wherein said first binding moiety specifically binds to a first antigen present on a cytotoxic effector T (Tc) cell, and said second binding moiety specifically binds to the IL-23 receptor specific subunit (IL23R).

Within the meaning of the present invention, the term "construct" refers to any chemical entity so long as it exhibits the desired binding activity. Thus, the term "construct" is used in the broadest sense and specifically covers protein-based molecules, including recombinant antibodies and fragments thereof comprising one or more antibody-based domains or binding fragments thereof. Specific examples include, but are not limited to, monoclonal chimeric antibodies, humanized antibodies, single-chain diabodies and the like. Furthermore, the term "comprise" as used within the present invention, for example in conjunction with the term "construct", encompasses both "includes" and "consists of".

The term "bispecific", as used herein, is intended to refer to a construct having two different antigen specificities and, optionally, other binding moieties that bind to their respective binding partners, such as a moiety that binds to an Fc receptor or a tag for detection and/or purification. This means that a bispecific construct is capable of simultaneously binding to at least one antigen "A" and at least one antigen "B", wherein A and B are not the same. Thus, whilst having two different antigen specificities, a bispecific construct of the present invention does not necessarily have only two binding moieties, one for each targeted antigen, but may also include more than two binding moieties. Furthermore, the term "antigen", as used herein, is to be interpreted in a broad sense and includes any target moiety that is bound by the binding moieties of the bispecific construct of the present invention.

As used in the present invention, the terms "specific" or "specifically" are intended to mean that the first and second binding moieties are able to discriminate between their respective target molecules (i.e. between the first and second antigen) and/or one or more reference molecule(s). Thus, in its broadest sense, "specific binding" or "specifically binding" refers to the first and second binding moieties' ability to discriminate between the first antigen on the surface of a Tc cell and the IL23R second antigen on the surface of a target cell and/or between other target molecules that are related to or not related to the first antigen and/or the second antigen (i.e., IL23R).

The binding specificity of a specific binding moiety can be determined as known in the art using, for example, surface plasma resonance (SPR), western blot, enzyme-linked immunosorbent assay (ELISA), radioimmunoassay (RIA or IRMA), enhanced chemiluminescence (ECL), and peptide scan analysis.

If an ELISA assay is used, the scoring can be carried out by means of a standard color development reaction, for example by using horseradish peroxidase (HRP)-conjugated second antibodies in a HRP, H2O2, tetramethyl benzidine system. The optical density of the color development in the reaction vessel (e.g. well) at a given wavelength is a measure of the binding specificity. A typical background signal (negative reaction) may be about 0.1 OD, whereas a typical signal for a positive reaction may be about 1.0 OD or higher, resulting in a signal to noise ratio of 10:1 or higher. Typically, the determination of the binding specificity is carried out using a set of about three to five unrelated biomolecules, such as milk powder, BSA, transferrin and the like, rather than using only a single reference biomolecule.

In particular, the present invention relates to a method for the treatment of cancer comprising IL23R-expressing tumor cells, comprising administering to a subject, particularly a human patient, an effective amount of the bispecific construct of the present invention.

The term "effective amount" is defined as set out below in Section [0085]. Typically, an effective amount of the bispecific construct of the present invention is administered in form of the above-described pharmaceutical composition. Suitable administration routes include, but are not limited to, topical and parenteral administration, in particular subcutaneous and intravenous injection. The administration regimen is not particularly limited and includes, for example, continuous infusion over one week, two weeks or four weeks.

The cancer to be treated includes, but is not limited to, colorectal cancer, lung cancer, breast cancer, nasopharyngeal cancer, oral cancer, esophageal cancer, pancreatic cancer, B-cell lymphomas, and T-cell lymphomas, including adult T-cell lymphoma leukemia (ATLL), acute myeloid lymphoma (AML), diffuse large B-cell lymphoma (DLBCL), follicular lymphoma (FL), pediatric acute lymphoblastic lymphoma (B-ALL), angioimmunoblastic T-cell lymphoma (AITL), anaplastic large-cell lymphoma (ALCL), T-/natural killer-cell lymphomas, and peripheral T-cell lymphoma (PTCL). In particular embodiments the cancer is selected from colorectal cancer, lung cancer, breast cancer, nasopharyngeal cancer, oral cancer, esophageal cancer, B-cell lymphomas, and T-cell lymphomas such as adult T-cell lymphoma leukemia (ATLL), angioimmunoblastic T-cell lymphoma (AITL), anaplastic large-cell lymphoma (ALCL), T-/natural killer-cell lymphomas, and peripheral T-cell lymphoma (PTCL).

The balance between interleukin (IL)-23 and IL-12 plays an important role in regulating the anti-tumor immune response. IL-23 and IL-12 are heterodimeric cytokines that share one of their domains (p40). While IL-12—consisting of the two subunits p35 and p40—has been found to have antitumor effects, IL-23 that is composed of p40 and p19, seems to promote growth of certain tumors by direct effects on tumor cells and by indirect mechanisms creating a tumor supportive inflammatory microenvironment. IL-12 drives the development of IFN-γ producing Th1 cells, which are crucial for the antitumor immunity (Dunn, G. P. et al. 2006. Nat. rev. Immunol: 6; 836-848; Colombo, M. P. and Trinchieri, G. 2002. Cytokine Growth Factor Rev; 13:155-168). IL-12 and IFN-γ are able to inhibit the expansion of intratumoral T regulatory cells (Tregs) that antagonize the activity of Th1 cells, as well as angiogenesis in the tumor microenvironment, thus enhancing tumor control (Cao, X et al. 2009. Cancer Res; 69:8700-8709). In line with a converse effect of IL-23 in the tumor microenvironment, IL-23 suppresses IL-12-dependent IFN-γ secretion in T cells (Sieve, A. N. et al. 2010. Eur. J. Immunol; 40; 2236-2247). In the gut, IL-23 produced by dendritic cells (DCs) in response to microbial products, cellular stress and cell death, may drive the formation of Th17 cells instead of an antitumor Th1 response. These Th17 cells in turn also produce IL-23, which may inhibit the immune surveillance activity mediated by cytotoxic T cells by potentially preventing their ability to infiltrate into the tumor (Ngiow, S. F. 2013. Trend in Immunology; 34:548-555) and to affect antitumor and antimetastatic functions of NK cells (Teng, M. W. et al. 2010 PNAS; 107:8328-8333). In line with the view that IL-23 signaling may have effects supporting tumor formation and/or growth in certain tumors is the finding that mice deficient only in IL-12 signaling show increased tumor growth, while mice deficient for both, IL-12 and IL-23 signaling, show no increased risk of developing tumors (Street, S. E. et al. 2002. J. Exp. Med; 196:129-134; Airoldi, I, et al. 2005. Blood; 106:3846-3853). Furthermore, mice specifically deficient for IL-23 signaling—but not for IL-12 signaling—were found to be almost completely resistant to tumor formation and showed attenuated tumor growth (Langowski, J. L. et al. 2008. Nature; 442:461-465; Teng, M. W. et al. 2010 PNAS; 107:8328-8333). In a recent study it was further found that the coadministration of an anti-CD40 antibody stimulating T-cells together with an anti-IL-23 antibody attenuating the Th17 response showed better efficacy as compared to either antibody alone (von Scheidt, B. et al. 2014. Cancer Res; DOI: 10.1158/0008-5472. CAN-13-1646), possibly by shifting the balance from Th17 to Th1. In the human situation, independent clinical studies have reported that serum concentrations of IL-23 are increased in cancer patients in comparison with healthy individuals (Li, J. et al. 2012. PLoS ONE; 7:e46264; Gangemi, S. et al. 2012. J. Cell. Biochem; 113:2122-2125; Ljujic, B. et al. 2010. Arch. Med. Res; 41:182-189; He, S. et al. 2011. Int. J. Mol. Sci; 12:7424-7437; Fukuda, M, et al. 2010. Int. J. Oncol; 36:1355-1365). For example in pancreatic cancer, elevated IL-23 levels correlated with disease stage and in breast cancer with poor prognosis (He, S. et al. 2011. Int. J. Mol. Sci; 12:7424-7437). In primary hepatocellular carcinoma (HCC) higher IL-23 levels in the cancer microenvironment have been associated with poor prognosis. Also in colorectal cancer serum IL-23 levels were increased in patients as compared to healthy donors (Stanilov, N. S. 2009. Labmedicine; 41:159-163). Further, Th17 gene expression profiles as well as Th17 cell infiltrations in colorectal cancer tissue samples were associated with drastically worse prognosis as opposed to Th1 gene expression or Th1 cell infiltration (Tosolini et al, Cancer Res 2011; 71:1263-1271). Collectively, these data suggest that IL-23 promotes tumorigenesis by driving protumor inflammation to suppress antitumor effector cells.

Human IL23R is predominantly found in activated memory T cells, natural killer (NK) cells, and innate lymphoid cells (ILCs), and at lower levels on monocytes, macrophages, and dendritic cells (DCs). Recently, direct effects of interleukin IL-23 on tumor cells have been described, suggesting that IL23R is expressed also on certain tumors. For example IL-23 was shown to have proproliferative effects on human oral squamous cell carcinoma (SSC) cell lines (Fukuda, M et al. 2010. Int. J. Oncol; 36:1355-1365; Fukuda, M et al. 2010. Mol. Med. Rep; 3:89-93) and non-small cell lung cancer (NSCLC) cell lines (Baird, A. M. et al. 2013. Lung Cancer; 79:83-90). Using genome-wide association studies, two sequence variants of IL23R have been associated with the risk of several solid cancers and the same polymorphisms have been found to predispose individuals to an increased risk of acute myeloid leukemia (AML) (Xu, Y, et al. 2013. J Gastroenterol; 48:125-131; Chu, H. et al. 2012. Int. J. cancer; 130:1093-1097; Chen, J. et al. 2010. mol. Carcinog; 49:862-868; Qian, X. et al. 2013. PLoS ONE; 8:e55473). IL23R expression was further found to be upregulated in primary tumor tissue of small cell lung cancer (SCLC), in lung andenocarcinoma (Li, J. et al. 2013. Carcinog; 34:658-666), in follicular lymphoma (FL) and diffuse large B cell lymphoma (DLBCL) (Cocco et al. Leukemia. 2012:26:1365-1374), in pediatric B-ALL (Cocco et al. Blood. 2010; 116:3887-3898) as well as in colorectal carcinoma (CRC) (Lan et al, Int J Colorectal Dis 2011; 26:1511-1518; Suzuki et al, Oncology Letters 2012; 4:199-204). In CRC a correlation between expression level and severity/metastasis was found (Carlsson et al, Br J Cancer 2012; 106:517-524).

Taken together, IL-23 seems to create an inflammatory microenvironment that on one hand favors tumor formation, growth and metastasis and on the other hand supports tumor immune escape by attenuating the Th1 antitumor response (see FIG. 1A). Preclinical studies with co-administration of anti-CD40 and anti-IL-23 antibodies have demonstrated that this "push" (anti-CD40 driven activation of T cells) and "pull" (anti-IL-23 driven attenuation of Th17 cells) is effective in certain tumor models. However, this approach does not specifically target cancer cells. Thus certain cancer cells are still likely to escape the enhanced Th1 response. And further, systemic activation of Th1 cells may lead to adverse effect, such as enhancing inflammatory processes. Other approaches using bispecific antibodies redirecting T cells to lyse cancer cells have demonstrated efficacy in different tumor models, also in solid tumors such as colorectal cancer (Lutterbuese, R. et al. 2010. PNAS; 107:12605-12610; Osada T. et al. 2010; British J Cancer; 102:124-133).

Here we present a novel approach aiming at optimally balancing efficacy and safety, by specifically targeting cancer cells on one hand and by locally stimulating the anti-tumor immune-response on the other hand. To achieve this, a bispecific anti-IL23RxCD3ε antibody is employed that acts through the mechanisms, illustrated in FIG. 1B:
  a) Redirecting CD3+ cytotoxic T cells to lyse IL23R expressing tumors;
  b) Stimulating CD3+Th1 cells specifically in the tumor microenvironment, as binding to target cells and consequently cross-linking of CD3ε binding domains is required for T cell stimulation;
  c) Redirecting CD3+ cytotoxic T cells to lyse IL23R expressing Th17 cells, thereby eliminating a major source of Th1 inhibitory cytokines;
  d) Redirecting CD3+ cytotoxic T cells to lyse IL23R expressing regulatory T (Treg) cells that inhibit the Th1 anti-tumor response; and
  e) Optionally: blocking IL-23 signaling by competing with IL-23 binding to its receptor IL23R.

In particular embodiments, said human patient is a patient, which has a high Th17 response.

In the context of the present invention, the term "high Th17 response" refers to a situation, where a patient either shows increased Th17 gene expression or increased counts of Th17 cells. An increased Th17 gene expression may be shown by increased levels of Th17 gene mRNA in the tumor tissue when compared to normal distant control tissue. In colorectal cancer such increase is at least 2-fold, particularly 4-fold and most particularly 5- to 6-fold for the genes IL17A and RORC (see Tosolini et al., Cancer Res 2011; 71:1263-1271) between tumor tissue and normal distant mucosa. An increased count of Th17 cells may be seen in the tumor tissue or in the tumor adjacent tissue compared to distant control tissue. In colorectal cancer, such increased counts are observed in the center or at the invasive margin, particularly in both the center and the invasive margin of the tumor (see Tosolini et al., loc. cit.)

In a second aspect, the present invention relates to a bispecific construct having at least one first binding moiety and at least one second binding moiety. The first and second binding moieties specifically bind to a first antigen and a second antigen, respectively. The first antigen is an antigen present on the surface of an immune effector cell, namely a cytotoxic effector T (Tc) cell (also known as cytotoxic T lymphocyte (CTL) or T killer cell). The second antigen is the IL-23 receptor specific subunit, IL23R, present on the surface of a target cell.

Within the present invention, one target cell type is typically a pathogenic cell, in particular a pathogenic T cell, more particularly a T cell expressing the transcription factor RORγ(t). RORγ(t) promotes thymocyte differentiation into pro-inflammatory Th17 cells and also plays a role in inhibiting apoptosis of undifferentiated T cells and promoting their differentiation into Th17 cells, possibly by down-regulating the expression of the Fas ligand and IL-2, respectively. In particular embodiments, the cells are selected from the group consisting of IL-17 producing T cells (Th17 cells), γδ T cells, natural killer T (NKT) cells and invariant natural killer (iNK) cells. Most particularly, the target cells within the present invention are selected from Th17 cells and γδ T cells.

Another target cell type within the present invention is a tumor cell, particularly a tumor cell expressing IL23R. IL23R expression has for example been shown for epithelial cancers such as colon carcinoma (CRC), small-cell lung cancer (SCLC), adenocarcinoma (AC) of the lung, as well as on various B- and T-cell tumors, exemplified by diffuse large B-cell lymphoma (DLBCL), follicular lymphoma (FL), pediatric B-ALL and acute myeloid lymphoma (AML).

In particular such embodiments, said bispecific construct has at least one first binding moiety directed against an antigen present on the surface of an immune effector cell, namely a cytotoxic effector T (Tc) cell (also known as cytotoxic T lymphocyte (CTL) or T killer cell), and at least a second binding moiety directed against the IL-23 receptor specific subunit, IL23R, present on the surface of a tumor cell, wherein said bispecific construct is also able to eliminate Th17 cells and to stimulate a Th1 response. In particular such embodiments, said first antigen is CD3, particularly CD3ε.

The first and second binding moieties are not structurally limited so long as they specifically bind to the desired first and second antigens. However, the first and second binding moieties generally consist of or are formed of one or more oligo- or polypeptides or parts thereof. Particularly, the first and second binding moieties are antibody-based binding moieties, which typically comprise at least one antibody variable domain or binding fragment thereof.

In a particular embodiment of the present invention, the first binding moiety specifically binds to a first antigen selected from CD3 and CD28. The CD3 protein is associated with the T cell receptor (TCR) and required for T cell activation. CD3 is a complex of one CD3γ, one CD3δ and two CD3ε chains which, together with the TCR and the ζ-chain, form the TCR receptor complex. CD28 is one of the molecules expressed on T cells that provide co-stimulatory signals required for T cell activation. Stimulation through CD28 can provide a potent co-stimulatory signal to T cells.

In a particular embodiment of the present invention, the first binding moiety binds specifically to CD3, more particularly to the epsilon chain of CD3 (CD3ε), and most particularly to an agonistic epitope of CD3ε. The term "agonistic epitope", as used herein, means (a) an epitope that, upon binding of the bispecific construct of the present invention, optionally upon binding of several bispecific constructs on the same cell, allows said bispecific constructs to activate TCR signaling and induce T cell activation, and/or (b) an epitope that is solely composed of amino acid residues of the epsilon chain of CD3 and is accessible for binding by the bispecific construct of the present invention, when presented in its natural context on Tc cells (i.e. surrounded by the TCR, the CD3γ chain, etc.), and/or (c) an epitope that, upon binding of the bispecific construct of the present invention, does not lead to stabilization of the spatial position of CD3ε relative to CD3γ.

In another particular embodiment of the present invention, instead of binding to Tc cells, the first binding moiety specifically binds to a component of the complement system, such as C1q. C1q is a subunit of the C1 enzyme complex that activates the serum complement system.

In an alternative embodiment, the present invention also contemplates the use of a first binding moiety that specifically binds to an Fc receptor, in particular to an Fc gamma receptor (FcγR). The FcγR may be a FcγRIII present on the surface of natural killer (NK) cells or one of FcγRI, FcγRIIA, FcγRIIB1, FcγRIIB2, and FcγRIIIB present on the surface of macrophages, monocytes, neutrophils and/or dendritic cells.

In such embodiment, the first binding moiety particularly is an Fc region or functional fragment thereof. In the present context, a "functional fragment" refers to a fragment of an antibody Fc region that is still capable of binding to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis. Particularly, a functional Fc fragment is capable of competitively inhibiting the binding of the original, full-length Fc portion to an FcR such as the activating FcγRI. Particularly, a functional Fc fragment retains at least 30%, 40%, 50%, 60%, 70%, 80%, 90% or 95% of its affinity to an activating FcγR.

Within such embodiment of the present invention, the Fc region or functional fragment thereof is particularly an enhanced Fc region or functional fragment thereof. The term "enhanced Fc region", as used herein, refers to an Fc region that is modified to enhance Fc receptor-mediated effector-functions, in particular antibody-dependent cell-mediated cytotoxicity (ADCC), complement-dependent cytotoxicity (CDC), and antibody-mediated phagocytosis. This can be achieved as known in the art, for example by altering the Fc region in a way that leads to an increased affinity for an activating receptor (e.g. FcγRIIIA (CD16A) expressed on natural killer (NK) cells) and/or a decreased binding to an inhibitory receptor (e.g. FcγRIIB1/B2 (CD32B)).

Suitable alterations within the present invention include altering glycosylation patterns, in particular afucosylation (also referred to as "defucosylation"), mutations (point mutations, deletions, insertions) and fusions with oligo- or polypeptides. Known techniques for altering glycosylation patterns include overexpression of heterologous β1,4-N-acetylglucosaminyltransferase III in the antibody-producing cell (known as the Glycart-Roche technology) and knocking out of the gene encoding α-1,6-fucosyltransferase (FUT8) in the antibody-producing cell (the Potelligent technology from Kyowa Hakko Kirin). Specific examples of enhancing mutations in the Fc part include those described in Shields et al., J. Biol. Chem. 276:6591-6604 (2001), which is incorporated herein in its entirety.

In accordance with the present invention, the bispecific construct is particularly designed in such a way that the killing of IL23R-expressing target cells by Tc cells is highly efficient. Such efficient killing generally involves the ability of the bispecific construct to effectively redirect Tc cells to lyse IL23R-expressing target cells. The term "efficient", as used herein, means that the bispecific construct of the present invention typically shows an in vitro $EC_{50}$ ranging from 10 to 500 ng/ml, and is able to induce redirected lysis of about 50% of the target cells through Tc cells at a ratio of Tc cells to target cells of from 1:1 to 50:1, particularly from 1:1 to 15:1, more particularly from 2:1 to 10:1. As used herein above and below, the terms "about" and "approximately" refer to ±10% of the indicated value or range.

Furthermore, the bispecific construct of the present invention is particularly capable of cross-linking a stimulated or an (otherwise) unstimulated Tc cell and the target cell in such a way that the target cell is lysed. This offers the advantage that no generation of target-specific T cell clones or common antigen presentation by dendritic cells is required for the bispecific construct to exert its desired activity. In fact, the bispecific construct of the present invention is particularly capable of redirecting Tc cells to lyse the target cells in the absence of other activating signals. More particularly, if the first binding moiety of the bispecific construct specifically binds to CD3, particularly to CD3ε, signaling through CD28 and/or IL-2 is not required for redirecting Tc cells to lyse the target cells. The high potential to activate non-target specific and/or unstimulated Tc cells is considered to be an important feature of the bispecific construct of the present invention and is believed to contribute to the efficient killing of target cells.

The present invention further contemplates that the first and second binding moieties are particularly arranged relative to each other in such a manner that the bispecific construct preferentially binds to the first antigen present on a Tc cell and, simultaneously, to the second antigen (i.e., IL23R) present on the target cell, but is essentially not capable of simultaneous binding to a single cell that co-expresses both the first antigen and IL23R (e.g. an IL-17 expressing cytotoxic (Tc17) cell).

Methods for measuring the preference of the bispecific construct to simultaneously bind to two cells are within the normal capabilities of a person skilled in the art. For example, the bispecific construct of the present invention may be contacted with a mixture of $CD3^+/IL23R^-$ cells and $CD3^+/IL23R^+$ cells or with a mixture of $CD3^+/IL23R^-$ cells and $CD3^+/IL23R^+$ cells. The number of bispecific construct-positive single cells and the number of cells crosslinked by bispecific constructs may then be assessed by microscopy or fluorescence-activated cell sorting (FACS) as known in the art. About the same number of observed bispecific cross-linked cells in both set-ups indicate that the bispecific construct of the present invention does not, or does essentially not, bind to a single target cell exhibiting both the CD3 and IL23R antigen on its surface. Alternatively, the apparent binding activity avidity may be determined. If simultaneous binding to a single target cell is not, or is essentially not, possible, the apparent binding activity of the bispecific construct for $IL23R^+/CD3^-$ or $IL23R^-/CD3^+$ cells on one side and $IL23R^+/CD3^+$ cells on the other side will be about the same. If, however, simultaneous binding to a single target cell is possible, the apparent binding activity of the bispecific construct for IL23R+/CD3+ cells will be higher than that for IL23R+/CD3− or IL23R−/CD3+ cells due to avidity effects.

In a particular embodiment of the present invention, the bispecific construct has a structure where the first and second binding moieties are arranged relative to each other in such a manner that the part of the first binding moiety recognizing the first antigen and the part of the second binding moiety recognizing the second antigen project, relative to the center of the bispecific construct, outward in essentially opposite directions. The term "center" particularly relates to the center of geometry (COG). Without being bound by any theory, it is believed that this structure of the bispecific construct of the present invention avoids the undesired double-binding to a single target cell as outlined above. The term "essentially", as used in the present context, means that said part of the first binding moiety and said part of the second moiety are arranged, relative to the center of the bispecific construct, at an angle of 135° or more up to 180°.

The structure of the bispecific construct is particularly also characterized in that the angle α between a first vector v1 from the center of geometry (COG) of the entire bispecific construct to the COG of the first paratope of the first binding moiety and a second vector v2 from the COG of the entire bispecific construct to the COG of the second paratope of the second binding moiety is approximately within the range of $135°<\alpha<180°$, more particularly within the range of $150°<\alpha<180°$, and most particularly within the range of $160°<\alpha<180°$. The term "paratope", as used herein, refers to the portions of the first and second binding moieties that directly interact with the first and second antigens, respectively.

In the context of the present invention, the first binding moiety and/or the second binding moiety is an antibody-based binding moiety, particularly an antibody-based binding moiety comprising a heavy chain variable domain (VH) or binding fragment thereof, more particularly an antibody-based binding moiety comprising a heavy chain variable domain (VH) or binding fragment thereof and a light chain variable domain (VL) or binding fragment thereof. The term "binding fragment", as used herein, refers to a portion of a given domain, region or part, which is (either alone or in combination with another domain, region or part thereof) still functional, i.e. capable of binding to the first or second antigen recognized by the bispecific construct.

Typically, a binding fragment within the meaning of the present invention retains at least 10% of its native antigen binding activity (i.e. of its antigen binding activity as a monospecific construct) when comprised in a bispecific construct of the present invention. Particularly, a binding fragment retains at least 25%, 50%, 60%, 70%, 80%, 90%, 95%, or 99% of its native antigen binding activity, or maintains or even exceeds the full native antigen binding activity, although any binding fragment with sufficient affinity to exert the desired biological effect (i.e. lysing/killing of target cells by Tc cells) will be useful. It is also intended that a "binding fragment" within the meaning of the present invention includes variants having conservative amino acid substitutions that retain their binding activity to the extent defined above and, particularly, do not substantially alter their binding or biological activity.

In another particular embodiment of the present invention, the bispecific construct is an antibody format selected from the group consisting of a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tri(a) body, bispecific Fab2, di-miniantibody, tetrabody, scFv-Fc-scFv fusion, di-diabody, DVD-Ig, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), and Knob-into-Holes (KiHs) (bispecific IgGs prepared by the KiH technology) and DuoBodies (bispecific IgGs prepared by the Duobody technology). Particularly suitable for use herein is a single-chain diabody (scDb), in particular a bispecific monomeric scDb.

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for IL23R.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. The middle linker L2 particularly is a peptide of 10-40 amino acids, more particularly 15-30 amino acids, and most particularly 20-25 amino acids.

In a particular embodiment of the present invention, the VH domain of the first and second antibody-based binding moieties of the bispecific construct comprises rabbit heavy chain complementarity determining regions (CDRs) grafted onto human heavy chain framework (FW) regions, and the VL domain of the first and second antibody-based binding moieties of the bispecific construct comprises rabbit light chain CDRs grafted onto human light chain FW regions.

The heavy chain and light chain CDRs of the first antibody-based binding moiety are particularly derived from a rabbit antibody obtained by immunization of a rabbit with the full-length epsilon chain of human CD3 the full-length, CD28 or the full-length C1q. The immunization with the full-length chain of CD3ε, CD28 or C1q is suitably conducted by DNA immunization of a rabbit with a plasmid encoding the full-length chain of human CD3ε, CD28 or C1q, or, alternatively, with the purified extracellular domain of the epsilon chain of CD3, or with the purified extracellular chain of CD28, or with the purified C1q. Further, the heavy chain and light chain CDRs of the second antibody-based binding moiety are particularly derived from a rabbit antibody obtained by immunization of a rabbit either with the purified extracellular domain of IL23R or with a plasmid expressing the full-length IL23R.

The bispecific constructs of the present invention can be produced using any convenient antibody manufacturing method known in the art (see, e.g., Fischer, N. & Leger, O., Pathobiology 74:3-14 (2007) with regard to the production of bispecific constructs; Hornig, N. & Färber-Schwarz, A., Methods Mol. Biol. 907:713-727, 2012, and WO 99/57150

A2 with regard to bispecific diabodies and tandem scFvs). In addition, exemplary anti-IL23R and anti-CD3ε antibody sequences are disclosed in EP 2 395 025 and EP 1 348 715, respectively. Specific examples of suitable methods for the preparation of the bispecific construct of the present invention further include, inter alia, the Genmab (see Labrijn et al., Proc. Natl. Acad. Sci. USA 110:5145-5150 (2013)) and Merus (see de Kruif et al., Biotechnol. Bioeng. 106:741-750 (2010)) technologies. Methods for production of bispecific antibodies comprising a functional antibody Fc part are also known in the art (see, e.g., Zhu et al., Cancer Lett. 86:127-134 (1994)); and Suresh et al., Methods Enzymol. 121:210-228 (1986)).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/yeast display) (see, e.g., Chames & Baty, FEMS Microbiol. Letters 189:1-8 (2000)), and the combination of the antigen-binding domains or fragments or parts thereof of two different monoclonal antibodies to give a bispecific construct using known molecular cloning techniques.

The bispecific constructs of the present invention are particularly humanized in order to reduce immunogenicity and/or to improve stability. Techniques for humanization of antibodies are well-known in the art. For example, one technique is based on the grafting of complementarity determining regions (CDRs) of a xenogeneic antibody onto the variable light chain VL and variable heavy chain VH of a human acceptor framework (see, e.g., Jones et al., Nature 321:522-525 (1986); and Verhoeyen et al., Science 239:1534-1536 (1988)). In another technique, the framework of a xenogeneic antibody is mutated towards a human framework. In both cases, the retention of the functionality of the antigen-binding portions is essential (Kabat et al., J. Immunol. 147:1709-1719 (1991)).

The bispecific constructs of the present invention may alternatively comprise one or more binding moieties based on non-antibody based binding domains. Specific examples of suitable methods for the preparation of the bispecific construct of the present invention further include, inter alia, the DARPin technology (Molecular Partners AG), the adnexin technology (Adnexus), the anticalin technology (Pieris), and the Fynomer technology (Covagen AG).

In a particular embodiment of the present invention, the bispecific construct is PRO165 (SEQ ID NO: 7), or a functionally active variant of PRO165.

In the context of the present invention, the term "functionally active variant of PRO165" refers to a bispecific construct based on the VL and VH regions of PRO165, wherein (i) said bispecific construct maintains the functional activity of PRO165, i.e. wherein a first VH/VL pair specifically binds to CD3ε, and wherein a second VH/VL pair specifically binds to the IL-23 receptor specific subunit (IL23R), and wherein (ii) said VL and VH regions comprise at least one sequence variation compared the VL and VH regions of PRO165. In particular embodiments, the CDR sequences of said functionally active variant are at least 70%, particularly at least 80%, more particularly at least 90% homologous to the CDR sequences of the VL and VH regions of PRO165. Most particularly, the CDR sequences of said functionally active variant are at least 90% identical and at least 95% homologous to the CDR sequences of the VL and VH regions of PRO165. In particular such embodiments, at least the CDR3 regions of the VH regions of said functional variant are identical to the corresponding CDR3 regions of PRO165. In more particular embodiments, all CDR regions of said functional variant are identical to the corresponding CDR regions of PRO165.

In another aspect, the present invention relates to a nucleic acid or multiple (i.e. more than one) nucleic acids encoding the bispecific construct of the present invention. If the bispecific construct is a single-chain construct, e.g. a polypeptide or protein, a single nucleic acid codes for the bispecific construct. However, if the bispecific construct comprises two or more polypeptides, the bispecific construct of the present invention may also be encoded by two or more separate nucleic acids. The nucleic acid molecule(s) according to the invention can be any nucleic acid molecule, particularly a DNA or RNA molecule, for example cDNA or mRNA. They can be naturally occurring molecules or produced through genetic engineering or chemical synthesis. They may be single-stranded molecules, which either contain the coding or the non-coding strand, or double-stranded molecules.

In a particular embodiment of the present invention, said nucleic acid or nucleic acids encode the bispecific construct PRO165 (SEQ ID NO: 7), or a functionally active variant thereof.

The nucleic acid(s) of the present invention may be produced by any suitable method as known to those skilled in the art. The nucleic acids of the present invention can, for example, be synthesized by the phosphoramidite method or the like, or can be produced by polymerase chain reaction (PCR) using specific primers. Furthermore, methods for introducing a desired mutation into certain nucleotide sequence, such as site-directed mutagenesis techniques, are well-known to a person skilled in the art.

In a further aspect, the present invention relates to a vector or multiple vectors comprising the nucleic acid(s) of the present invention. When comprised within a vector, in particular a plasmid, the nucleic acid(s) particularly is (are) DNA. The types of vectors used in the present invention are not particularly limited. For example, the vector may be a vector which replicates autonomously, such as a plasmid, or may be a vector which is integrated into the genome of a host cell when introduced into the host cell and is replicated along with the chromosome. Particularly, the vector used in the present invention is an expression vector, in particular an expression plasmid. In an expression vector, elements necessary for transcription, such as a promoter, are operatively linked to the DNA nucleic acid(s) of the present invention.

Examples of promoters which are operative in bacterial cells include PR or PL promoters of phage lambda, lac, trp or tac promoter of *Escherichia coli*, and the like. Examples of mammalian promoters include SV40 promoter, MT-1 (metallothionein gene) promoter, adenovirus 2 major late promoter, and the like. Furthermore, exemplary promoters for use in insect cells include polyhedrin promoter, P10 promoter, baculovirus immediate early gene 1 promoter, and the like. Moreover, suitable promoters for yeast host cells include a promoter derived from yeast glycolysis system genes, TPI1 promoter and the like. Other promoters suited for different expression systems are known in the art.

Further, if necessary, the DNA of the present invention may be operatively linked to a suitable terminator, such as a human growth hormone terminator or a TPI1 ADH3 fungal host terminator. The recombinant vector of the present invention may also have an element such as a polyadenylation signal (e.g., derived from SV40), a transcription enhancer sequence (e.g., a SV40 enhancer), or a translation enhancer sequence (e.g., encoding adenovirus VA RNA).

The recombinant vector of the present invention is also typically provided with a DNA sequence which enables the vector to replicate inside the host cell, and an example thereof for mammalian cells is an SV40 origin of replication. Furthermore, the recombinant vector of the present invention may also contain a selectable marker. Examples of a selectable marker include, inter alia, drug resistance genes such as ampicillin, kanamycin, tetracycline, chloramphenicol, neomycin, and hygromycin. Methods for connecting the nucleic acid(s) of the present invention with a promoter and, as desired, other regulatory sequences such as a terminator and/or a secretion signal sequence, and inserting these into a suitable vector are known to those skilled in the art.

In a particular embodiment of the present invention, said vector or vectors comprise a nucleic acid or nucleic acids, which encode(s) the bispecific construct PRO165 (SEQ ID NO: 7), or a functionally active variant thereof.

In yet another aspect, the present invention relates to a host cell or multiple host cells that are not identical, comprising the vector(s) of the present invention. The host cell(s) into which the recombinant vector of the present invention is (are) introduced is (are) not particularly limited and include any prokaryotic or eukaryotic cell which can express the vector of the present invention. Examples of suitable host cells include bacteria (e.g., *Bacillus* spp., *Streptomyces* spp., and *Escherichia coli*), mammalian cells (e.g., HEK293, HeLa, COS, BHK, CHL, and CHO cells), insect cells (e.g., baculovirus expression system), yeast cells (*Saccharomyces* spp. or *Schizosaccharomyces* spp., in particular *Saccharomyces cerevisae* and *Saccharomyces kluyveri*), and other fungal cells (e.g., *Aspergillus, Neurospora*). Particularly, the cells are bacterial cells, in particular *Escherichia coli* cells.

A multiple polypeptide chain bispecific construct can be made in a single host cell expression system wherein the host cell produces each chain of bispecific construct and assembles the polypeptide chains into a multimeric structure to form the bispecific construct, followed by recovery of the bispecific construct from the host cell. Alternatively, the separate polypeptide chains of the desired bispecific construct can be made in separate expression host cells, separately recovered from the respective host cells, and then mixed in vitro under conditions permitting the formation of the multi-subunit bispecific constructs as known in the art.

Methods for introducing the vector of the present invention into suitable host cells are known in the art and include the protoplast method, the competent cell method (for bacterial host cells), electroporation, the phosphate calcium method, lipofection (for mammalian cells or for insect cells/baculovirus system), electroporation, the spheroplast method, and the lithium acetate method (for yeast and other fungal host cells).

In yet a further aspect, the present invention relates to a method for producing the bispecific construct of the present invention, comprising providing a host cell or host cells of the present invention, culturing said host cell or said host cells and collecting the bispecific construct from the cell culture. In the culturing step, the host cell(s) of the present invention is (are) cultured in a suitable culture medium under conditions permitting expression of the bispecific construct of the present invention. The medium used to culture the cells may be any conventional medium suitable for growing the host cells, such as minimal or complex media containing appropriate supplements. Alternatively, the present invention relates to a method for producing the bispecific construct of the present invention, comprising providing a nucleic acid or nucleic acids according to the present invention, or a vector or vectors according to the present invention, expressing said nucleic acid or nucleic acids or said vector or vectors, particularly in an in vitro transcription/translation system (see, for example, Yin et al., Mabs 2012 Mar. 1; 4(2) 217-25), and collecting said bispecific construct from the expression system.

In the step of collecting the bispecific construct from the cell culture, the produced bispecific construct is recovered by conventional methods for isolating and purifying a protein, including separating the host cells from the medium by centrifugation or filtration, precipitating the proteinaceous components of the supernatant or filtrate by means of a salt, e.g. ammonium sulphate, and purification by a variety of chromatographic procedures, e.g. ion exchange chromatography, gel filtration chromatography, affinity chromatography or the like. In a case where the bispecific complex forms insoluble inclusion bodies, for example when using *E. coli* as host cell, the inclusion bodies may be first solubilized in denaturant, followed by a refolding step in accordance with procedures well known in the art.

In still another aspect, the present invention relates to a pharmaceutical composition comprising the bispecific construct of the present invention and a pharmaceutically acceptable carrier. As used herein, the term "pharmaceutically acceptable" refers to those compounds or substances which are, within the scope of sound medical judgment, suitable for contact with the tissues of mammals, especially humans, without excessive toxicity, irritation, allergic response and other problem complications. The term "carrier", as used herein, relates to a diluent, adjuvant, excipient or vehicle whereby the active ingredient is administered. Pharmaceutically acceptable carriers for use herein can be, for example, sterile liquids or dispersions. Particular carriers are those suited for intravenous, subcutaneous or topical administration, including sterile aqueous and non-aqueous solutions or suspensions for parenteral administration, as discussed in Remington: The Science and Practice of Pharmacy, 20th Edition (2000).

The pharmaceutical composition generally includes an effective amount of the bispecific construct of the present invention. Within the present invention, the term "effective amount" refers to the amount of a compound sufficient to effect beneficial or desired therapeutic results. A therapeutically effective amount can be administered in one or more administrations, applications or dosages and is not intended to be limited to a particular formulation or administration route. Also, the pharmaceutical composition may include one or more additional active substances that are co-administered with the bispecific construct of the present invention. In addition, the pharmaceutical composition may contain additional pharmaceutically acceptable substances, for example pharmaceutical acceptable excipients such as solubilizing agents, surfactants, tonicity modifiers and the like.

Furthermore, the dosage form of the pharmaceutical composition of the present invention is not particularly limited but particularly is a parenteral formulation, such as an aqueous or non-aqueous solution or dispersion for injection or infusion, or a formulation suited for topical administration. Another particular dosage form is a formulation containing the bispecific construct of the present invention formulated in a controlled or sustained or delayed release matrix. Further, the pharmaceutical composition may also be contained in an implantable device that releases the bispecific construct over time.

In still a further aspect, the present invention relates to the use of the bispecific construct of the present invention in the treatment of an inflammatory and/or autoimmune disease. In particular, the present invention relates to a method for the treatment of an inflammatory and/or autoimmune disease, comprising administering to a subject, particularly a human patient, an effective amount of the bispecific construct of the present invention. The meaning of the term "effective amount" is as defined herein above. Typically, an effective amount of the bispecific construct of the present invention is administered in form of the above-described pharmaceutical composition. Suitable administration routes include, but are not limited to, topical and parenteral administration, in particular inhalation, subcutaneous injection, intravenous injection, and injection into the cerebrospinal fluid. The administration regimen is not particularly limited and includes, for example, bi-weekly, monthly, once every other month, once every third, sixth or ninth month and once-a-year or single application administration schemes.

The inflammatory and/or autoimmune disease may be rheumatoid arthritis, ankylosing spondylitis, psoriasis, psoriatic arthritis, ulcerative colitis, Crohn's disease, systemic lupus erythematosus, juvenile diabetes, autoimmune uveitis, and multiple sclerosis, Parkinson's disease, Alzheimer's disease, and ischemia-reperfusion injury.

EXAMPLES

Example 1: Cloning of Bispecific Antibody Construct

A bispecific construct $V_HA$-L1-$V_LB$-L2-$V_HB$-L3-$V_LA$ (wherein the $V_LA$ and $V_HA$ domains jointly form the antigen binding site for CD3ε, and $V_LB$ and $V_HB$ jointly form the antigen binding site for IL23R) can be assembled by cloning $V_LA$ and $V_HA$ from the humanized anti-CD3ε antibody domain comprised in antibody bscCD19xCD3 (see EP 1 348 715 A2, FIG. 8, nucleotides 1258-1575, and nucleotides 847-1203, respectively), and $V_LB$ and $V_HB$ from the humanized anti-IL23R antibody 20D7 (see EP 2 395 025 A1, SEQ ID NOs: 9 and 4, respectively) with linkers L1 and L3 each consisting of the amino acid sequence GGGGS ($G_4S$) and the middle linker L2 consisting of the amino acid sequence GGGGSGGGGSGGGGSGGGGS ($G_4S$)$_4$ into an expression vector suitable for expression in *E. coli*, including an N-terminal signal sequence for secretion of the bispecific construct into the periplasm of the *E. coli* host cells T, using the techniques described in Holliger et al., Proc. Natl. Acad. Sci USA 90:6444-6448 (1993), Kipriyanov et al., J. Mol. Biol. 293:41-56 (1999) and Brüsselbach et al., Tumor Targeting 4:115-123 (1999).

Example 2: Expression Level of IL23R on Cancer Cell-Lines

The data available in the public domain suggest that IL23R may be upregulated in certain tumors. However, the available information is not sufficient to validate IL23R as a suitable marker to target cancer cells by a bispecific anti-IL23RxCD3ε antibody format, as neither the absolute expression level, nor the specificity of expression nor the penetrance of IL23R upregulation across different tumor samples are known. To further study the suitability of IL23R as a label for the targeted lysis of tumor cells, we assessed the expression level of IL23R both, on collection of primary cancer tissues, as well as on a broad spectrum of tumor cell-lines. Surprisingly, IL23R mRNA expression levels were elevated in most primary tissue samples from colorectal cancers. Similarly, elevated IL23R mRNA expression was found in all 129 CRC cell-lines studied. In agreement with these findings, IL23R was highly upregulated in all six colorectal cancer cell-lines studied as well as on the A549 lung adenocarcinoma cell-line also on a protein level as assessed by flow-cytometry (FIG. 2 and FIG. 3). Quantification of IL23R copies per cell revealed an expression level of about 10,000-88,000 copies per CRC cell (Table 1). Remarkably, we found strong expression of IL23R protein also on cell-lines that were published to be negative for the validated tumor markers CEA and EGFR, both targets against which bispecific T cell redirecting antibody therapeutics are currently in development (Osada, T. et al. 2010. British Journal of Cancer; 101:124-133; Lutterbuese, R. et al. 2010. PNAS; 107:12605-12610). Our data suggest that IL23R is a tumor marker that is specifically upregulated in most colorectal cancers, and that a bispecific anti-IL23RxCD3ε antibody for the targeted lysis of CRC cells has potential also in patients that are refractory to anti-CEA or anti-EGFR therapies. Interestingly, we found similar IL23R mRNA expression levels also in a variety of leukemia and lymphoma cell-lines and confirmed elevated IL23R protein expression in all cell lines tested (FIG. 4).

TABLE 1

| IL23R molecules expressed on the surface of cancer cell-lines. | | | |
|---|---|---|---|
| sample | ΔMFI * | S/N * | ABC * |
| COLO 678 | 17476 | 172.33 | 88'302 |
| DLD-1 | 13874 | 134.40 | 68'763 |
| HCT 116 | 1539 | 9.79 | 10'553 |
| HT-29 | 15540 | 65.21 | 74'865 |
| LS-174T | 8866 | 51.38 | 47'011 |
| SW 480 | 18985 | 138.57 | 77'428 |
| A549 | 1604 | 15.32 | 11'864 |
| TF-1 | 12410 | 74.43 | 67'904 |
| 697 | 468 | 10.64 | 5'734 |
| KIT225 | 1694 | 17.13 | 15'094 |
| DB | 563 | 3.51 | 5'677 |
| SU-DHL-4 | 113 | 3.4 | 1'441 |

ΔMFI, difference in mean fluorescence intensity, and S/N, Signal to background ratio between anti-IL23R antibody and isotype control. ABC, antigen binding capacity as determined by regression to reference standard beads.

Example 3: Identification of Monoclonal Rabbit Antibodies Binding to Human Interleukin (IL)-23 Receptor A total of 475 monoclonal B-cells producing antibodies specifically binding to interleukin-23 receptor were isolated from immunized rabbits using flow-cytometry-based single-cell sorting, the principles of which are well known to the expert and are for example described by Lalor et al Eur J Immunol. 1992; 22.3001-2011. Monoclonal B cell culture supernatants were first subjected to ELISA screening for binding to human IL23R ECD. In a second step, cross-reactivity to IL23R from mouse and cynomolgus monkey was assessed. Further, the affinity to human and cynomolgus IL23R was assessed using the surface plasmon resonance (SPR) technology (Table 2). The median equilibrium dissociation constant (KD) of those 475 monoclonal antibodies to human IL23R was 6.3E-11M. Five percent of these antibodies bound with an estimated KD below 4.3E-13M. A total of 92 clones selected either for their high affinity or their cross-reactivity to cynomolgus and/or mouse, were subjected to PCR amplification and sequencing of their variable domains.

The sequencing of the obtained rabbit IgG clones resulted in 68 complete sets of light and heavy chain variable domains (VL and VH). These sets of rabbit variable domains were analyzed by sequence alignment to identify unique clones and to group the sequences into clusters based on sequence homology. This alignment of the VL and VH domains was performed based on the joint amino acid sequences of both domains. The analysis led to the identification of 58 unique clones. In addition to the alignment of the variable domains, the set of sequences of the six complementarity determining regions (CDRs) of each rabbit IgG clone were compared between different clones to identify unique sets of CDRs. In total 58 unique sets of rabbit CDRs, corresponding to 58 independent clones, were identified. These 58 CDR sets were aligned using the multiple alignment tool COBALT and a phylogenetic tree was generated with the Neighbor Joining algorithm as shown in FIG. 5. Twenty three clones from different clusters were selected based on their affinity for human, cynomolgus and mouse IL23R for recombinant production and further characterization with the aim to proceed with high sequence diversity.

Example 4: Heterologous Production of Monoclonal Rabbit Antibodies

Following the selection of the clones (described above) rabbit antibodies were expressed and purified for further characterization. The cloning of the corresponding light and heavy chain variable domains entailed the in-vitro ligation of the DNA fragments into a suitable mammalian expression vector. These expression vectors contained consensus sequences for the constant domains of the rabbit IgG light and heavy chains to allow for the assembly and secretion of fully functional rabbit monoclonal IgGs upon co-expression. Subsequent to the vector construction the sequence of the resulting constructs was confirmed again and the plasmid DNA was amplified and purified for mammalian cell transfections. The expression vectors for the rabbit antibody heavy and light chains were transfected into a mammalian suspension cell line for transient heterologous expression by a lipid-based transfection reagent. The conditions like the ratio of heavy to light chain vector were optimized for robust expression levels of secreted monoclonal IgG. The expression culture was cultivated for 7 days in a shaking incubator. At the end of the heterologous expression period the cell culture supernatant was harvested by centrifugation and decanting. Subsequently the secreted rabbit IgGs were affinity purified by Protein A beads. The IgG loaded beads were washed and the purified antibodies were eluted by a pH shift. The elution fractions were analyzed by sodium dodecyl sulfate polyacrylamide gel electrophoresis (SDS-PAGE), UV absorbance at 280 nm and size-exclusion high performance liquid chromatography (SE-HPLC) to verify identity, content and purity.

Example 5: Characterization of Purified Monoclonal Rabbit Anti-IL23R Antibodies

The affinity of the 23 purified rabbit monoclonal antibodies towards IL23R from human, cynomolgus monkey and mouse origin was determined by SPR measurements. The respective results are given in Table 2 below:

TABLE 2

| Clone ID IgG | Human IL23R | | | Cyno IL23R | | | Mouse IL23R | | |
| --- | --- | --- | --- | --- | --- | --- | --- | --- | --- |
| | $k_a$ $[M^{-1} s^{-1}]$ | $k_d$ $[s^{-1}]$ | $K_D$ $[M]$ | $k_a$ $[M^{-1} s^{-1}]$ | $k_d$ $[s^{-1}]$ | $K_D$ $[M]$ | $k_a$ $[M^{-1} s^{-1}]$ | $k_d$ $[s^{-1}]$ | $K_D$ $[M]$ |
| 12-01-A08 | NB | NB | NB | ND | ND | ND | NB | NB | NB |
| 12-01-F09 | 1.80E+05 | 9.12E−05 | 5.07E−10 | 1.23E+05 | 5.37E−03 | 4.38E−08 | NB | NB | NB |
| 12-02-E05 | 2.15E+05 | <1.0E−06 | <4.66E−12 | 1.03E+05 | 1.93E−04 | 1.89E−09 | NB | NB | NB |
| 12-04-H09 | 1.74E+05 | 7.59E−05 | 4.37E−10 | 4.63E+05 | 7.71E−03 | 1.66E−08 | NB | NB | NB |
| 12-06-A05 | 1.53E+05 | 1.10E−05 | 7.17E−11 | 1.88E+04 | 8.23E−05 | 4.39E−09 | 5.48E+04 | 4.23E−05 | 7.72E−10 |
| 12-06-E01 | 1.18E+05 | 5.66E−05 | 4.82E−10 | 7.99E+04 | 1.14E−03 | 1.43E−08 | 1.80E+05 | 3.64E−03 | 2.02E−08 |
| 12-06-E03 | 6.58E+04 | 2.32E−05 | 3.53E−10 | 9.57E+04 | 7.31E−05 | 7.64E−10 | 8.91E+04 | 1.20E−03 | 1.35E−08 |
| 12-06-F06 | 2.83E+05 | 1.61E−05 | 5.70E−11 | 1.98E+05 | 5.98E−03 | 3.02E−08 | 2.67E+05 | 2.48E−03 | 9.31E−09 |
| 12-08-E06 | 9.72E+04 | 5.44E−05 | 5.60E−10 | 6.00E+04 | 2.49E−05 | 4.15E−10 | NB | NB | NB |
| 12-09-F05 | 1.33E+05 | 4.00E−06 | 3.00E−11 | 1.30E+05 | 4.54E−05 | 3.49E−10 | 8.46E+04 | 1.42E−03 | 1.68E−08 |
| 12-10-A06 | NB | NB | NB | ND | ND | ND | NB | NB | NB |
| 12-19-F08 | 2.29E+05 | 2.50E−05 | 1.10E−10 | 2.22E+05 | 1.33E−04 | 6.00E−10 | 2.45E+05 | 3.34E−04 | 1.36E−09 |
| 13-05-H06 | NB | NB | NB | NB | NB | NB | NB | NB | NB |
| 13-10-A03 | NB | NB | NB | NB | NB | NB | NB | NB | NB |
| 14-03-B01 | 2.79E+05 | <1E−06 | <3.58E−12 | 3.31E+05 | 4.82E−05 | 1.46E−10 | NB | NB | NB |
| 14-05-A11 | 2.26E+05 | <1E−06 | <4.43E−12 | 2.52E+05 | 8.46E−05 | 3.36E−10 | NB | NB | NB |
| 14-06-H08 | 3.34E+05 | 9.92E−06 | 2.97E−11 | 4.58E+05 | 3.17E−06 | 6.92E−12 | NB | NB | NB |
| 14-07-H07 | 2.50E+05 | 1.59E−05 | 6.33E−11 | 2.70E+05 | 3.00E−05 | 1.11E−10 | NB | NB | NB |
| 14-08-E05 | 2.17E+05 | 5.98E−05 | 2.76E−10 | 2.45E+05 | 3.79E−05 | 1.55E−10 | NB | NB | NB |
| 14-11-D07 | 4.14E+05 | 1.98E−07 | 4.78E−13 | 4.48E+05 | <1E−06 | <2.23E−12 | 2.23E+05 | 3.34E−04 | 1.50E−09 |
| 14-13-D08 | 2.06E+05 | <1E−06 | <4.85E−12 | 3.07E+05 | 2.77E−05 | 9.02E−11 | NB | NB | NB |
| 14-14-E08 | 5.19E+05 | <1E−06 | <1.93E−12 | 5.12E+05 | 1.58E−05 | 3.08E−11 | NB | NB | NB |
| 14-17-B09 | 6.77E+05 | 7.49E−05 | 1.11E−10 | 3.53E+05 | 1.16E−04 | 3.30E−10 | 8.08E+04 | <1E−06 | <1.24E−11 |

Example 6: Engineering and Characterization of a Humanized Single-Chain Fv Fragment The humanization of rabbit antibody clone 14-11-D07 comprised the transfer of the rabbit CDRs onto Numab's proprietary scFv acceptor framework of the Vκ1/VH3 type. In this process the amino acid sequence of the six CDR regions was identified on the rabbit antibody donor sequence as described elsewhere (Borras, L. et al. 2010. JBC; 285: 9054-9066) and grafted into the Numab acceptor scaffold sequence. Two variants were generated, where the variant sc01 resulted from exclusively engrafting complementarity determining regions (CDRs) onto the human acceptor variable domain scaffold, while variant sc02 contains further mutations also in the human framework sequence. The two resulting humanized scFvs were characterized for their binding affinity towards IL23R from human, cynomolgus and mouse origin (see Table 3). As no significant difference in affinity was detectable for the two variants, 14-11-D07-sc01 was chosen to be engineered in the scDb format because in this variant no rabbit amino acids were engrafted from the rabbit donor framework sequences to the human acceptor sequence, thus minimizing the risk to provoke anti-drug immune response in humans following application.

The midpoint of transition for the thermal unfolding of the tested constructs was determined by Differential Scanning Fluorimetry (DSF), essentially as described by Niesen (Niesen et al., Nat Protoc. 2 (2007) 2212-21). The DSF assay is performed in a qPCR machine (e.g. MX3005p, Agilent Technologies). The samples were diluted in buffer (citrate-phosphate pH 6.4, 0.25 M NaCl) containing a final concentration of 5×SYPRO orange in a total volume of 25 μL. Samples were measured in duplicate and a temperature ramp from 25-96° C. programmed. The fluorescence signal was acquired and the raw data was analyzed with the GraphPad Prism (GraphPad Software Inc.; results see Table 5).

TABLE 5

The midpoint of transition for the thermal unfolding was determined for all constructs by differential scanning fluorimetry

| | | Thermal Unfolding | |
|---|---|---|---|
| scDb ID | anti-IL23R | anti-CD3 | Tm |
| PRO165 | 14-11-D07-sc01 | clone 6 | 65.3 |

TABLE 3

| | human IL23R | | | cyno IL23R | | | mouse IL23R | | |
|---|---|---|---|---|---|---|---|---|---|
| Clone ID scFv | $k_a$ [$M^{-1}s^{-1}$] | $k_d$ [$s^{-1}$] | $K_D$ [M] | $k_a$ [$M^{-1}s^{-1}$] | $k_d$ [$s^{-1}$] | $K_D$ [M] | $k_a$ [$M^{-1}s^{-1}$] | $k_d$ [$s^{-1}$] | $K_D$ [M] |
| 14-11-D07-sc01 | 2.24E+06 | 2.59E−04 | 1.16E−10 | 2.92E+06 | 3.61E−04 | 1.24E−10 | 1.89E+06 | 4.18E−03 | 2.21E−09 |
| 14-11-D07-sc02 | 1.17E+06 | 1.13E−04 | 9.60E−11 | 1.55E+06 | 2.05E−04 | 1.33E−10 | 8.30E+05 | 1.39E−03 | 1.68E−09 |

Example 7: Engineering and Characterization of a Bispecific Single-Chain Diabodies (scDb)

With the aim to redirect CD3ε+ T cells to lyse IL23R expressing target cells, a bispecific antibody fragment of the so-called single-chain diabody (scDb) format was engineered. This construct termed PRO165 contains the VH and VL of the anti-IL23R scFv 14-11-D07-sc01, as well as the VH and VL of a humanized rabbit anti-CD3ε antibody (clone 6). The anti-CD3ε binding domain was selected a) for its high affinity to human CD3ε, b) for its excellent cross-reactivity to CD3ε from cynomolgus origin, c) for its outstanding stability and resistance towards aggregation, and d) because this CD3ε binder activates T cells exclusively upon cross-linking—as it may for example occur following binding to target cells—thereby minimizing the risk for potential side-effects due to unspecific activation of T cells.

Affinities of the anti-IL23R and anti-CD3ε binding moieties towards human, cyno and mouse IL23R, and human and mouse CD3ε, respectively were measured by SPR (Table 4).

Example 8: Targeted Lysis of IL23R Expressing Cells

To study potency of the scDbs to induce specific lysis of target cells, IL23R expressing cells were co-cultivated with human CD8+ T cells in presence of increasing concentrations of the respective scDb. Lysis of cells in dependence of the scDb concentration was assessed by measuring fluorescence intensity of celltox-green intercalated into DNA. The EC50 of PRO165 for the respective cell-line is given in Table 6.

TABLE 6

| | | | $EC_{50}$ of specific target cell lysis [nM] | | | |
|---|---|---|---|---|---|---|
| | | IL23R binding | | | | |
| ID | Format | moiety | DLD-1 | SW-480 | TF-1 | CHO |
| PRO165 | scDb | 14-11-D07-sc01 | 45.4 | 71.7 | 39.8 | no lysis |

TABLE 4

| | human IL23R | | | human CD3ε | | |
|---|---|---|---|---|---|---|
| scDb ID | $k_d$ [$s^{-1}$] | $K_D$ [M] | $K_D$ [M] | $k_a$ [$M^{-1}s^{-1}$] | $k_d$ [$s^{-1}$] | $K_D$ [M] |
| PRO165 | 1.26E−03 | 1.16E−08 | 1.82E−10 | 1.09E+05 | 1.26E−03 | 1.16E−08 |

Methods:
1. Assessment of IL23R Expression Levels on Cell Lines

For the detection of IL23R on the cell membrane, living cells were stained with 5 μg/mL of a biotinylated polyclonal goat anti-IL23R antibody (R&D Systems, Cat. No. BAF1400). As background control, a polyclonal goat IgG isotype was used (R&D Systems, Cat. No. BAF108). Binding of goat polyclonal antibodies to cells was in turn detected by a Phycoerythrin-(PE)-labeled streptavidin (Southern Biotech, Cat. No. 7100-09S). PE fluorescence intensity of stained cells was measured by flow-cytometry (FACS aria III, Becton Dickinson). In order to quantify IL23R molecules per cell anti-human IgG Quantum™ Simply Cellular® (QSC) microspheres (Bangs Laboratories, Cat. No. 816) loaded with human IL-23R Fc chimera (R&D Systems, Cat. No. 1400-IR-050) were used as a reference standard. The mean fluorescence intensity (MFI), reflecting the signal intensity at the geometric mean, was measured for both, the goat IgG isotype control as well as for the goat anti-IL23 R antibody. The difference between the MFI of the specific antibody and isotype control antibody (ΔMFI) was calculated. The normalized MFI was calculated by dividing the MFI obtained with the anti-IL23R antibody by the MFI of the idiotype control. To quantify IL23R molecules on the cell surface the specific Antibody Binding Capacity (ABC) of cells was calculated by regression of the respective MFI to the standard curve generated by use of Quantum™ Simply Cellular® (QSC) microspheres. Calculations were performed in the lot-specific QuickCal® template. To compare unspecific binding the ABC value of cells stained with negative control antibody were subtracted from ABC value of cells stained with the specific antibody.

2. SPR Assay for Determination of Binding Kinetics and Species Cross-Reactivity of Monoclonal Antibodies in Culture Supernatant Binding affinities of monoclonal rabbit anti-IL23R antibodies in sort supernatants were measured by surface plasmon resonance (SPR) using a MASS-1 SPR instrument (Sierra Sensors). For affinity measurements (run in DPBS with 0.05% Tween) an antibody specific for the Fc region of rabbit IgGs (Bethyl Laboratories, Cat. No. A120-111A) was immobilized on a sensor chip (SPR-2 Affinity Sensor, Amine, Sierra Sensors) using a standard amine-coupling procedure. After immobilization, rabbit monoclonal antibodies in culture supernatants were captured by the anti-rabbit IgG antibody while a second immobilized channel served as a control where the capture was replaced by negative supernatant (cultured media that does not contain sorted cells). Human IL23R extracellular domain (ECD) (produced on request by Trenzyme, Germany) at 90 nM was injected into both flow cells for 3 min and dissociation of the protein from the captured IgG on the sensor chip was allowed to proceed for 5 min. In a similar manner the affinities for cynomolgus and mouse IL23R ECD (both at 90 nM, produced on request by Trenzyme) were measured. The apparent dissociation (kd) and association (ka) rate constants and the apparent dissociation equilibrium constant (KD) were calculated with the MASS-1 analysis software (Analyzer, Sierra Sensors) using one-to-one Langmuir binding model.

3. SPR Assay for Determination of Binding Kinetics and Species Cross-Reactivity of Purified Monoclonal Antibodies Binding affinities of purified monoclonal rabbit anti-IL23R antibodies were measured in a similar setup as the sort supernatants, except that the sort supernatants were replaced by purified IgGs. A sensor chip (SPR-2 Affinity Sensor, High Capacity Amine, Sierra Sensors) was immobilized by the same procedure, and purified monoclonal antibodies at a concentration of 0.5 μg/ml (diluted in HEPES running buffer: 0.01 M HEPES, 0.15 M NaCl, 0.05% Tween) were captured by the anti-rabbit IgG antibody. No capture was done on the immobilized control channel. Two-fold serial dilutions of human IL23R extracellular domain ranging from 90 to 2.81 nM were injected into the flow cells for 3 min and dissociation of the protein from the captured IgG on the sensor chip was allowed to proceed for 5 min. After each injection cycle, surfaces were regenerated with a single 1 min injection of 10 mM glycine-HCl pH 1.5. In a similar manner the affinities for cynomolgus and mouse IL23R ECD were measured. The apparent dissociation (kd) and association (ka) rate constants and the apparent dissociation equilibrium constant (KD) were calculated with the MASS-1 analysis software (Analyzer, Sierra Sensors) using one-to-one Langmuir binding model.

4. SPR Assay for Determination of Binding Kinetics and Species Cross-Reactivity of Anti-IL23R scFvs Binding affinities of anti-IL23R scFvs were measured by surface plasmon resonance (SPR) using a MASS-1 SPR instrument (Sierra Sensors). For affinity measurements (done in HEPES running buffer: 0.01 M HEPES, 0.15 M NaCl, 0.05% Tween) an antibody specific for the Fc region of human IgGs (Bethyl Laboratories, Cat. No. A80-104A) was immobilized on a sensor chip (SPR-2 Affinity Sensor, High Capacity Amine, Sierra Sensors) using a standard amine-coupling procedure. After immobilization, 1 ug/ml recombinant human IL23R Fc chimera (R&D Systems, Cat. No. 1400-IR-050) was captured by the anti-human IgG antibody while a second immobilized channel served as a control where the capture was replaced by buffer. Two-fold serial dilutions of human scFvs ranging from 180 to 2.81 nM were injected into both flow cells for 3 min and dissociation of the scFvs from the chimera on the sensor chip was allowed to proceed for 700 sec. After each injection cycle, surfaces were regenerated with two 1 min injections of 10 mM glycine-HCl pH 1.5. In a similar manner the affinities for cynomolgus and mouse IL23R Fc chimera (R&D Systems, Cat. No. 1686-MR-050) was measured. The apparent dissociation (kd) and association (ka) rate constants and the apparent dissociation equilibrium constant (KD) were calculated with the MASS-1 analysis software (Analyzer, Sierra Sensors) using one-to-one Langmuir binding model.

5. SPR Assay for Determination of Binding Kinetics and Species Cross-Reactivity of Anti-CD3 x IL23R scDbs Binding affinities of anti-CD3 x IL23R scDbs were measured by surface plasmon resonance (SPR) using a MASS-1 SPR instrument (Sierra Sensors). For affinity measurements (done in HEPES running buffer: 0.01 M HEPES, 0.15 M NaCl, 0.05% Tween) to CD3, human heterodimeric single-chain CD3γδ extracellular domain (produced in-house) was immobilized on a sensor chip (SPR-2 Affinity Sensor High Capacity Amine, Sierra Sensors) using a standard amine-coupling procedure. Three-fold serial dilutions of scDbs ranging from 90 to 0.123 nM were injected into the flow cells for 3 min and dissociation of the protein from the immobilized CD3γδ on the sensor chip was allowed to proceed for 700 sec. After each injection cycle, surfaces were regenerated with a 1 min injection of 10 mM Glycine-HCl pH 2.0. In a similar manner the binding to cynomolgus CD3γδ (produced in-house) and mouse CD3δε (Sino Biologicals Inc., Cat. No. CT033-M2508H) was measured.

For affinity measurements to IL23R, human IL23R extracellular domain (produced on request by Trenzyme) was immobilized on a sensor chip (SPR-2 Affinity Sensor High Capacity Amine, Sierra Sensors) using a standard amine-coupling procedure. Two-fold serial dilutions of scDbs ranging from 90 to 5.6 nM were injected into the flow cells for 3 min and dissociation of the protein from the immobilized IL23R on the sensor chip was allowed to proceed for 720 sec. After each injection cycle, surfaces were regenerated with a 1 min injection of 10 mM Glycine-HCl pH 2.0. The apparent dissociation (kd) and association (ka) rate constants and the apparent dissociation equilibrium constant (KD) are calculated with the MASS-1 analysis software (Analyzer, Sierra Sensors) using one-to-one Langmuir binding model.

6. scDb Mediated Lysis of IL-23R Expressing Cells by Cytotoxic T Cells

For the assessment of the potential of bispecific anti-CD3 x IL-23R scDbs to induce target cell lysis human IL-23R expressing cell lines were used. Colon carcinoma DLD-1 or SW480, and erythroleukemia TF-1 were used as target cell lines Unstimulated human CD8+ T-cells isolated as described above were used as effector cells. Target cells were labeled with cell tox green dye (Promega) according to the manufacturer's instructions. Cell lysis was monitored by the CellTox™ green cytotoxicity assay (Promega). The assay measures changes in membrane integrity that occur as a result of cell death. The assay uses an asymmetric cyanine dye that is excluded from viable cells but preferentially stains the dead cell DNA. When the dye binds DNA in compromised cells, its fluorescence properties are substantially enhanced. Viable cells produce no appreciable increases in fluorescence. Therefore, the fluorescence signal produced by the binding interaction with dead cell DNA is proportional to cytotoxicity. Similarly as described above, labeled IL-23R cells (5'000 cells/well) were incubated with CD8+ cytotoxic T-cells at an effector:target ratio of 40:1 in presence of 3-fold serially diluted scDbs (starting concentration 180 nM) in 96 well microtiter plates. To assess unspecific lysis of cells that do not express the target, T-cells were co-incubated with labeled wild-type CHO cells. Fluorescence intensity was analyzed after 48 h of incubation using a multi-mode microplate reader (FlexStation 3, Molecular Devices). Data were analyzed using a four-parameter logistic curve fit using the SoftMak☐ Pro data analysis Software (Molecular Devices), and the molar concentration of scDb required to induce half maximal target cell lysis ($EC_{50}$) was derived from dose-response curves.

In order to specifically track the fate of target cells, target cells were stained with CellVue® Claret Far Red Fluorescent (Sigma-Aldrich, Cat. No. MINCLARET-1KT) in a concentration of 5 nM Dye according to the manufacturer's instructions. Apoptosis/necrosis was monitored using the Annexin V Apoptosis Detection Kit FITC (eBioscience, Cat. No. 88-8005-74) according to the manufacturer's instructions (concentration of dyes: 100 µL/mL Annexin V and 2 µg/mL Propidium iodide). Stained IL-23R cells (5'000 cells/well) were incubated with CD8+ cytotoxic T-cells at an effector:target ratio of 40:1 in presence of serially diluted scDbs (starting concentration 180 nM) in 96 well microtiter plates. To assess unspecific lysis of cells that do not express the target, T-cells were co-incubated with labeled CHO cells. Fluorescence intensities were analyzed after 48 h of incubation using a flow cytometer (FACS aria III, Becton Dickinson). Data were analyzed by discriminate target from effector cells using the far red fluorescent dye (CellVue® Claret. Far Red Fluorescent). Target cells were gated into live cells and early-/late-stage apoptotic, necrotic cells by Annexin V and PI fluorescence. The data obtained were analyzed using a four-parameter logistic curve fit using the SoftMax® Pro data analysis Software (Molecular Devices), and the molar concentration of scDb required to induce half maximal target cell lysis (EC50) was derived from dose-response curves.

7. Construct Design and Manufacturing of scDb Constructs

The single-chain diabody constructs were designed by arranging the variable domains in a VLA-L1-VHB-L2-VLB-L3-VHA configuration. In these constructs the VLA and VHA domains jointly form the binding site for IL23R while the VLB and VHB domains jointly form the binding site for CD3ε. The peptide linkers L1-L3 connecting the variable domains are constructed of the glycine/serine repeats. The two short linkers L1 and L3 are composed of a single G4S repeat, whereas the long linker L2 is composed of the sequence (G4S)4. The nucleotide sequences encoding the various anti-IL23RxCDE3ε scDb constructs were de novo synthesized and cloned into an adapted vector for E. coli expression that is based on a pET26b(+) backbone (Novagen).

The expression construct was transformed into the E. coli strain BL12 (DE3) (Novagen) and the cells were cultivated in 2YT medium (Sambrook, J., et al., Molecular Cloning: A Laboratory Manual) as a starting culture. Expression cultures were inoculated and incubated in shake flasks at 37° C. and 200 rpm. Once an OD600 nm of 1 was reached protein expression was induced by the addition of IPTG at a final concentration of 0.5 mM. After overnight expression the cells were harvested by centrifugation at 4000 g. For the preparation of inclusion bodies the cell pellet was resuspended in IB Resuspension Buffer (50 mM Tris-HCl pH 7.5, 100 mM NaCl, 5 mM EDTA, 0.5% Triton X-100). The cell slurry was supplemented with 1 mM DTT, 0.1 mg/mL Lysozyme, 10 mM Leupeptin, 100 µM PMSF and 1 µM Pepstatin. Cells were lysed by 3 cycles of ultrasonic homogenization while being cooled on ice. Subsequently 0.01 mg/mL DNAse was added and the homogenate was incubated at room temperature for 20 min. The inclusion bodies were sedimented by centrifugation at 15000 g and 4° C. The IBs were resuspended in IB resuspension Buffer and homogenized by sonication before another centrifugation. In total a minimum of 3 washing steps with IB Resuspension Buffer were performed and subsequently 2 washes with IB Wash Buffer (50 mM Tris-HCl pH 7.5, 100 mM NaCl, 5 mM EDTA) were performed to yield the final IBs.

For protein refolding the isolated IBs were resuspended in Solubilization Buffer (100 mM Tris/HCl pH 8.0, 6 M Gdn-HCl, 2 mM EDTA) in a ratio of 5 mL per g of wet IBs. The solubilization mixture was incubated for 30 min at room temperature until DTT was added at a final concentration of 20 mM and the incubation was continued for another 30 min. After the solubilization was completed the solution was cleared by 10 min centrifugation at 21500 g and 4° C. The refolding was performed by rapid dilution at a final protein concentration of 0.3 g/L of the solubilized protein in Refolding Buffer (typically: 100 mM Tris-HCl pH 8.0, 5.0 M Urea, 5 mM Cysteine, 1 mM Cystine). The refolding reaction was routinely incubated for a minimum of 14 h. The resulting protein solution was cleared by 10 min centrifugation at 8500 g and 4° C. The refolded protein was purified by affinity chromatography on Capto L resin (GE Healthcare) followed by a size-exclusion chromatography on a Superdex 75 column (GE Healthcare). The proteins were formulated in native buffer (50 mM Citrate-Phosphate pH 6.4, 150 mM NaCl). The isolated monomer fraction was analyzed by size-exclusion HPLC, SDS-PAGE for purity and UV/Vis spectroscopy for protein content.

Sequence listing for PRO165:
VLA-L1-VHB-L2-VLB-L3-VHA

| SEQ ID | Type | Sequence |
|---|---|---|
| 1 | Linker L1 | GGGGS |
| 2 | Linker L2 | GGGGS GGGGS GGGGS GGGGS |
|   | Linker L3 | GGGGS |
| 3 | VL anti-IL23R 14-11-D07-sc01 | DIQMTQSPSSLSASVGDRVTITCQASENIYSFLA WYQQKPGKAPKLLIYSASKLAAGVPSRFSGSGS GTDFTLTISSLQPEDFATYYCQQTNRYSNPDIYN VFGQGTKLTVLG |
| 4 | VH anti-IL23R 14-11-D07-sc01 | EVQLVESGGGLVQPGGSLRLSCAASGIDFNSNY YMCWVRQAPGKGLEWIGCIYVGSHVNTYYANW AKGRFTISRDNSKNTVYLQMNSLRAEDTAVYYC ATSGSSVLYFKFWGQGTLVTVSS |
| 5 | VL anti-CD3 clone 6 | DIQMTQSPSSLSASVGDRVTITCQSSESVYNNKR LSWYQQKPGKAPKLLIYTASSLASGVPSRFSGS GSGTDFTLTISSLQPEDFATYYCQGEFTCSNADC FTFGQGTKLTVLG |
| 6 | VH anti-CD3 clone 6 | EVQLVESGGGLVQPGGSLRLSCAASGFPLSSYA MIWVRQAPGKGLEWIGMILRAGNIYYASWVKGR FTISRDNSKNTVYLQMNSLRAEDTAVYYCARRH YNREGYPIGIGDLWGQGTLVTVSS |
| 7 | PRO165 | DIQMTQSPSSLSASVGDRVTITCQASENIYSFLA WYQQKPGKAPKLLIYSASKLAAGVPSRFSGSGS GTDFTLTISSLQPEDFATYYCQQTNRYSNPDIYN VFGQGTKLTVLGGGGGSEVQLVESGGGLVQPG GSLRLSCAASGFPLSSYAMIWVRQAPGKGLEWI GMILRAGNIYYASWVKGRFTISRDNSKNTVYLQM NSLRAEDTAVYYCARRHYNREGYPIGIGDLWGQ GTLVTVSSGGGGSGGGGSGGGGSGGGGSDIQ MTQSPSSLSASVGDRVTITCQSSESVYNNKRLS WYQQKPGKAPKLLIYTASSLASGVPSRFSGSGS GTDFTLTISSLQPEDFATYYCQGEFTCSNADCFT FGQGTKLTVLGGGGGSEVQLVESGGGLVQPGG SLRLSCAASGIDFNSNYYMCWVRQAPGKGLEWI GCIYVGSHVNTYYANWAKGRFTISRDNSKNTVYL QMNSLRAEDTAVYYCATSGSSVLYFKFWGQGTL VTVSS |

We claim:

1. A bispecific construct comprising at least one first binding moiety and at least one second binding moiety, wherein said first binding moiety specifically binds to a first antigen present on a cytotoxic effector T (Tc) cell, wherein said first antigen is CD3, and said second binding moiety specifically binds to the IL-23 receptor specific subunit (IL23R) present on the surface of a target cell,
wherein said bispecific construct is an antibody format selected from the group of a bispecific T-cell engager (BiTE; tandem di-scFv), a tandem tri-scFv, a tri(a) body, a single-chain diabody (scDb), a tandem scDb (Tandab), a linear dimeric scDb (LD-scDb) and a circular dimeric scDb (CD-scDb) and comprises two variable heavy chain domains ($V_H$) or fragments thereof and two variable light chain domains ($V_L$) or fragments thereof connected by linkers L1, L2 and L3 in the order $V_HA$-L1-$V_LB$-L2-$V_HB$-L3-$V_LA$, $V_HA$-L1-$V_HB$-L2-$V_LB$-L3-$V_LA$, $V_LA$-L1-$V_LB$-L2-$V_HB$-L3-$V_HA$, $V_LA$-L1-$V_HB$-L2-$V_LB$-L3-$V_HA$, $V_HB$-L1-$V_LA$-

L2-$V_H$A-L3-$V_L$B, $V_H$B-L1-$V_H$A-L2-$V_L$A-L3-$V_L$B, $V_L$B-L1-$V_L$A-L2-$V_H$A-L3-$V_H$B or $V_L$B-L1-$V_H$A-L2-$V_L$A-L3-$V_H$B, wherein the $V_L$A and $V_H$A domains jointly form the antigen binding site for the first antigen, and $V_L$B and $V_H$B jointly form the antigen binding site for IL23R.

2. The bispecific construct of claim 1, wherein said first binding moiety specifically binds to the epsilon chain of CD3 (CD3ε).

3. The bispecific construct of claim 1, wherein the construct allows for efficient killing of said target cell by the Tc cell, wherein said Tc cell is a stimulated or an unstimulated Tc cell.

4. The bispecific construct of claim 1, wherein said first and second binding moieties are arranged relative to each other in such a manner that the part of the first binding moiety recognizing the first antigen and the part of the second binding moiety recognizing IL23R project, relative to the center of the bispecific construct, outward in essentially opposite directions.

5. The bispecific construct of claim 1, wherein the bispecific construct is PRO165 (SEQ ID NO: 7), or a functionally active variant of PRO165.

6. A method for producing the bispecific construct according to claim 1, comprising (i) providing a nucleic acid or nucleic acids encoding the bispecific construct according to claim 1 or a vector or vectors comprising said nucleic acid or nucleic acids, expressing said nucleic acid or nucleic acids or said vector or vectors and collecting said bispecific construct from the expression system, or (ii) providing a host cell or host cells comprising said vector or vectors, culturing said host cell or said host cells; and collecting said bispecific construct from the cell culture.

7. A pharmaceutical composition comprising the bispecific construct according to claim 1 and a pharmaceutically acceptable carrier.

8. The bispecific construct according to claim 1 for use in the treatment of an inflammatory and/or autoimmune disease.

9. The bispecific construct of claim 1, wherein said target cell is a pathogenic cell.

10. The bispecific construct of claim 9, wherein the pathogenic cell is a cell selected from the group of an IL-17 producing T cell (Th17 cell), a γδ T cell, a natural killer T (NKT) cell, an invariant natural killer (iNK) cell and an IL23R expressing tumor cell.

11. The bispecific construct of claim 10, wherein the pathogenic cell is a Th17 cell, a γδ T cell or an IL23R expressing tumor cell.

12. The bispecific construct of claim 1, wherein said first binding moiety specifically binds to an agonistic epitope of (CD3ε).

13. The bispecific construct of claim 1, wherein the bispecific construct is a bispecific monomeric scDb.

14. The bispecific construct of claim 1, wherein linker L1 is a peptide of 2-10 amino acids.

15. The bispecific construct of claim 1, wherein linker L3 is a peptide of 1-10 amino acids.

16. The bispecific construct of claim 1, wherein linker L2 is a peptide of 10-40 amino acids.

17. The bispecific construct of claim 8, for use in treatment of a human patient.

18. The bispecific construct of claim 8, wherein the inflammatory and/or autoimmune disease is selected from the group of rheumatoid arthritis, ankylosing spondylitis, psoriasis, psoriatic arthritis, ulcerative colitis, Crohn's disease, systemic lupus erythematosus, juvenile diabetes, autoimmune uveitis, multiple sclerosis, Parkinson's disease, Alzheimer's disease, and ischemia-reperfusion injury.

* * * * *